(12) United States Patent
Kellinger et al.

(10) Patent No.: US 12,391,929 B2
(45) Date of Patent: Aug. 19, 2025

(54) POLYMERASE-NUCLEOTIDE CONJUGATES FOR SEQUENCING BY TRAPPING

(71) Applicant: Element Biosciences, Inc., San Diego, CA (US)

(72) Inventors: Matthew Kellinger, San Diego, CA (US); Michael Previte, San Diego, CA (US); Molly He, San Diego, CA (US); Tyler Lopez, Winchester, CA (US)

(73) Assignee: Element Biosciences, Inc., San Diego, CA (US)

( * ) Notice: Subject to any disclaimer, the term of this patent is extended or adjusted under 35 U.S.C. 154(b) by 366 days.

(21) Appl. No.: 16/895,999

(22) Filed: Jun. 8, 2020

(65) Prior Publication Data
US 2020/0370113 A1    Nov. 26, 2020

Related U.S. Application Data

(63) Continuation of application No. PCT/US2020/034102, filed on May 21, 2020.

(60) Provisional application No. 62/852,876, filed on May 24, 2019.

(51) Int. Cl.
*C12N 9/12* (2006.01)
*C12Q 1/6869* (2018.01)

(52) U.S. Cl.
CPC .......... *C12N 9/1252* (2013.01); *C12Q 1/6869* (2013.01); *C12Y 207/07007* (2013.01)

(58) Field of Classification Search
CPC ............ C12Q 1/6869; C12Q 2525/197; C12Q 2525/125; C12N 9/1252; C12Y 207/07007
See application file for complete search history.

(56) References Cited

U.S. PATENT DOCUMENTS

| | | | |
|---|---|---|---|
| 7,871,771 B2 | 1/2011 | Fuller et al. |
| 7,960,116 B2 | 6/2011 | Eid et al. |
| 8,399,196 B2 | 3/2013 | Hoser |
| 8,632,975 B2 | 1/2014 | Vander Horn et al. |
| 8,652,781 B2 | 2/2014 | Korlach |
| 8,956,816 B2 | 2/2015 | Fedorov et al. |
| 9,222,132 B2 | 12/2015 | Drmanac |
| 9,279,154 B2 | 3/2016 | Previte et al. |
| 9,932,631 B1 | 4/2018 | Dambacher et al. |
| 9,951,385 B1 | 4/2018 | Vijayan et al. |
| 10,233,490 B2 | 3/2019 | Stapleton et al. |

(Continued)

FOREIGN PATENT DOCUMENTS

| CN | 217981206 U | 12/2022 |
| CN | 218974139 U | 5/2023 |

(Continued)

OTHER PUBLICATIONS

SPIE 2010 ("Optical Fiber Technology: Basics of Fibers" from the website of The International Society for Optics and Photonics; https://spie.org/samples/FG16.pdf) (Year: 2010).*
PCT/US2020/034102 International Search Report and Written Opinion dated Jul. 23, 2020.
Chen et al.: Optical biosensors: an exhaustive and comprehensive review. Analyst. 145(5):1605-1628 doi:10.1039/c9an01998g (Abstract) (2020).

(Continued)

*Primary Examiner* — Jeremy C Flinders
(74) *Attorney, Agent, or Firm* — Fenwick & West LLP; Heidi A. Erlacher; Jessica D. Cande

(57) ABSTRACT

Compositions and methods comprising the use of polymerase-nucleotide conjugates for nucleic acid sequencing and analysis applications are described.

15 Claims, 13 Drawing Sheets
(11 of 13 Drawing Sheet(s) Filed in Color)

(56) References Cited

U.S. PATENT DOCUMENTS

| | | |
|---|---|---|
| 10,655,176 B2 | 5/2020 | Stromberg et al. |
| 10,704,094 B1 | 7/2020 | Arslan et al. |
| 10,768,173 B1 | 9/2020 | Arslan et al. |
| 10,876,148 B2 | 12/2020 | Zhou et al. |
| 10,982,280 B2 | 4/2021 | Arslan et al. |
| 11,053,540 B1 | 7/2021 | Chen et al. |
| 11,060,138 B1 | 7/2021 | Chen et al. |
| 11,198,121 B1 | 12/2021 | Guo et al. |
| 11,200,446 B1 | 12/2021 | Zhou et al. |
| 11,220,707 B1 | 1/2022 | Arslan et al. |
| 11,236,388 B1 | 2/2022 | Arslan et al. |
| 11,248,254 B2 | 2/2022 | Dambacher et al. |
| 11,261,489 B2 | 3/2022 | Chen et al. |
| 11,339,433 B2 | 5/2022 | Chen et al. |
| 11,397,870 B2 | 7/2022 | Zhou et al. |
| 11,427,855 B1 | 8/2022 | Arslan et al. |
| 11,535,892 B1 | 12/2022 | Arslan et al. |
| 11,781,185 B2 | 10/2023 | Arslan et al. |
| 11,788,075 B2 | 10/2023 | Hentschel et al. |
| 11,795,504 B2 | 10/2023 | Chen et al. |
| 11,859,241 B2 | 1/2024 | Arslan et al. |
| 11,891,651 B2 | 2/2024 | Arslan et al. |
| 11,915,444 B2 | 2/2024 | Zhou et al. |
| 12,006,518 B2 | 6/2024 | Hentschel et al. |
| 12,091,657 B2 | 9/2024 | Kellinger et al. |
| 12,117,438 B2 | 10/2024 | Arslan et al. |
| 12,134,766 B2 | 11/2024 | Kellinger et al. |
| 12,139,727 B2 | 11/2024 | Ambroso et al. |
| 12,146,190 B2 | 11/2024 | Ghorbani et al. |
| 12,163,163 B2 | 12/2024 | Boothby-Hentschel et al. |
| 2011/0111975 A1 | 5/2011 | Schneider et al. |
| 2016/0032379 A1 | 2/2016 | Gloeckner et al. |
| 2016/0152972 A1 | 6/2016 | Stapleton et al. |
| 2017/0022553 A1 | 1/2017 | Vijayan et al. |
| 2017/0314064 A1 | 11/2017 | Iyidogan et al. |
| 2017/0314072 A1 | 11/2017 | Vijayan et al. |
| 2018/0044727 A1 | 2/2018 | Vijayan et al. |
| 2018/0155698 A1 | 6/2018 | Iyidogan et al. |
| 2018/0187245 A1 | 7/2018 | Dambacher et al. |
| 2018/0208983 A1 | 7/2018 | Dambacher et al. |
| 2018/0327829 A1* | 11/2018 | Mir .................. C12Q 1/6869 |
| 2019/0241945 A1 | 8/2019 | Malyshev et al. |
| 2019/0276884 A1 | 9/2019 | Stapleton et al. |
| 2020/0149095 A1 | 5/2020 | Arslan et al. |
| 2020/0179921 A1 | 6/2020 | Arslan et al. |
| 2020/0182866 A1 | 6/2020 | Arslan et al. |
| 2020/0216899 A1 | 7/2020 | Arslan et al. |
| 2020/0231964 A1 | 7/2020 | Ben-Yehezkel et al. |
| 2020/0248258 A1 | 8/2020 | Arslan et al. |
| 2020/0263230 A1 | 8/2020 | Zhou et al. |
| 2020/0347443 A1 | 11/2020 | Arslan et al. |
| 2021/0040534 A1 | 2/2021 | Zhou et al. |
| 2021/0072234 A1 | 3/2021 | Arslan et al. |
| 2021/0121882 A1 | 4/2021 | Guo et al. |
| 2021/0123098 A1 | 4/2021 | Previte et al. |
| 2021/0123911 A1 | 4/2021 | Arslan et al. |
| 2021/0139884 A1 | 5/2021 | Kellinger et al. |
| 2021/0139981 A1 | 5/2021 | Arslan et al. |
| 2021/0222238 A1 | 7/2021 | Chen et al. |
| 2021/0222239 A1 | 7/2021 | Chen et al. |
| 2021/0223161 A1 | 7/2021 | Chen et al. |
| 2021/0223178 A1 | 7/2021 | Guo et al. |
| 2021/0223530 A1 | 7/2021 | Guo et al. |
| 2021/0223531 A1 | 7/2021 | Guo et al. |
| 2021/0247389 A1 | 8/2021 | Arslan et al. |
| 2021/0269793 A1 | 9/2021 | Kellinger et al. |
| 2021/0318294 A1 | 10/2021 | Previte et al. |
| 2021/0318295 A1 | 10/2021 | Arslan et al. |
| 2021/0332416 A1 | 10/2021 | Chen et al. |
| 2021/0332430 A1 | 10/2021 | Arslan et al. |
| 2021/0333210 A1 | 10/2021 | Chen et al. |
| 2021/0333211 A1 | 10/2021 | Chen et al. |
| 2021/0373000 A1 | 12/2021 | Arslan et al. |
| 2021/0387184 A1 | 12/2021 | Guo et al. |
| 2022/0025457 A1 | 1/2022 | Chen et al. |
| 2022/0101039 A1 | 3/2022 | Zhou et al. |
| 2022/0170919 A1 | 6/2022 | Previte et al. |
| 2022/0186310 A1 | 6/2022 | Arslan et al. |
| 2022/0251643 A1 | 8/2022 | Chen et al. |
| 2022/0251644 A1 | 8/2022 | Chen et al. |
| 2022/0267842 A1 | 8/2022 | Chen et al. |
| 2022/0275437 A1 | 9/2022 | Stapleton et al. |
| 2022/0389408 A1 | 12/2022 | Ben-Yehezkel |
| 2022/0403351 A1 | 12/2022 | Ambroso et al. |
| 2022/0403352 A1 | 12/2022 | Ambroso et al. |
| 2022/0403353 A1 | 12/2022 | Ambroso et al. |
| 2022/0403445 A1 | 12/2022 | Arslan et al. |
| 2022/0403463 A1 | 12/2022 | Arslan et al. |
| 2022/0405523 A1 | 12/2022 | Zhou et al. |
| 2023/0038526 A1 | 2/2023 | Arslan et al. |
| 2023/0065693 A1 | 3/2023 | Arslan et al. |
| 2023/0167434 A1 | 6/2023 | Kellinger et al. |
| 2023/0193354 A1 | 6/2023 | Arslan et al. |
| 2023/0203564 A1 | 6/2023 | Arslan et al. |
| 2023/0235392 A1 | 7/2023 | Arslan et al. |
| 2023/0265400 A1 | 8/2023 | Hentshcel et al. |
| 2023/0265401 A1 | 8/2023 | Hentshcel et al. |
| 2023/0265402 A1 | 8/2023 | Hentshcel et al. |
| 2023/0279382 A1 | 9/2023 | Light et al. |
| 2023/0279483 A1 | 9/2023 | Light et al. |
| 2023/0295692 A1 | 9/2023 | Berti et al. |
| 2023/0296592 A1 | 9/2023 | Previte et al. |
| 2023/0296593 A1 | 9/2023 | Previte et al. |
| 2023/0323450 A1 | 10/2023 | Arslan et al. |
| 2023/0326064 A1 | 10/2023 | Zhou et al. |
| 2023/0326065 A1 | 10/2023 | Thompson et al. |
| 2023/0392144 A1 | 12/2023 | Price et al. |
| 2023/0392201 A1 | 12/2023 | Stapleton et al. |
| 2024/0011022 A1 | 1/2024 | Zhao et al. |
| 2024/0052398 A1 | 2/2024 | Previte et al. |
| 2024/0084380 A1 | 3/2024 | Arslan et al. |
| 2024/0117428 A1 | 4/2024 | Previte et al. |
| 2024/0191225 A1 | 6/2024 | Zhao et al. |
| 2024/0191278 A1 | 6/2024 | Arslan et al. |
| 2024/0200133 A1 | 6/2024 | Ghorbani et al. |
| 2024/0201088 A1 | 6/2024 | Ghorbani et al. |
| 2024/0230631 A1 | 7/2024 | Arslan et al. |
| 2024/0240249 A1 | 7/2024 | Zheng et al. |
| 2024/0287482 A1 | 8/2024 | Hentschel et al. |
| 2024/0382956 A1 | 11/2024 | Guo et al. |
| 2025/0019760 A1 | 1/2025 | Light et al. |
| 2025/0027144 A1 | 1/2025 | Arslan et al. |
| 2025/0034628 A1 | 1/2025 | Arslan et al. |

FOREIGN PATENT DOCUMENTS

| | | |
|---|---|---|
| WO | WO-2007070542 A2 | 6/2007 |
| WO | WO-2014142981 A1 | 9/2014 |
| WO | WO-2014171898 A2 | 10/2014 |
| WO | WO-2017117235 A1 | 7/2017 |
| WO | WO-2017184996 A1 | 10/2017 |
| WO | WO-2017190012 A1 | 11/2017 |
| WO | WO-2017223517 A1 | 12/2017 |
| WO | WO-2018045109 A1 | 3/2018 |
| WO | WO-2019033062 A2 | 2/2019 |
| WO | WO-2019241305 A1 | 12/2019 |
| WO | WO-2020102594 A1 | 5/2020 |
| WO | WO-2020102766 A2 | 5/2020 |
| WO | WO-2020118255 A1 | 6/2020 |
| WO | WO-2020223695 A1 | 11/2020 |
| WO | WO-2020242901 A1 | 12/2020 |
| WO | WO-2020243017 A1 | 12/2020 |
| WO | WO-2021061841 A1 | 4/2021 |
| WO | WO-2021146597 A1 | 7/2021 |
| WO | WO-2021236792 A1 | 11/2021 |
| WO | WO-2021252671 A2 | 12/2021 |
| WO | WO-2022026891 A1 | 2/2022 |
| WO | WO-2022047379 A1 | 3/2022 |
| WO | WO-2022094332 A1 | 5/2022 |
| WO | WO-2022266462 A2 | 12/2022 |
| WO | WO-2022266470 A1 | 12/2022 |
| WO | WO-2023004014 A1 | 1/2023 |
| WO | WO-2022266462 A3 | 5/2023 |
| WO | WO-2023107719 A2 | 6/2023 |

(56) References Cited

FOREIGN PATENT DOCUMENTS

| | | | |
|---|---|---|---|
| WO | WO-2023107720 A1 | 6/2023 |
| WO | WO-2023159219 A2 | 8/2023 |
| WO | WO-2023168443 A1 | 9/2023 |
| WO | WO-2023168444 A1 | 9/2023 |
| WO | WO-2023196924 A2 | 10/2023 |
| WO | WO-2023205707 A2 | 10/2023 |
| WO | WO-2023230278 A2 | 11/2023 |
| WO | WO-2023230279 A1 | 11/2023 |
| WO | WO-2023235865 A1 | 12/2023 |
| WO | WO-2023240040 A1 | 12/2023 |
| WO | WO-2023240093 A1 | 12/2023 |
| WO | WO-2023240128 A2 | 12/2023 |
| WO | WO-2023240230 A2 | 12/2023 |
| WO | WO-2024011145 A1 | 1/2024 |
| WO | WO-2024040058 A1 | 2/2024 |
| WO | WO-2024040068 A1 | 2/2024 |
| WO | WO-2024059550 A1 | 3/2024 |
| WO | WO-2024064631 A2 | 3/2024 |
| WO | WO-2024064912 A2 | 3/2024 |
| WO | WO-2024077165 A2 | 4/2024 |
| WO | WO-2024081805 A1 | 4/2024 |
| WO | WO-2024118641 A1 | 6/2024 |
| WO | WO-2024124008 A2 | 6/2024 |
| WO | WO-2024151556 A1 | 7/2024 |
| WO | WO-2024158927 A2 | 8/2024 |
| WO | WO-2024159166 A1 | 8/2024 |
| WO | WO-2024173403 A2 | 8/2024 |
| WO | WO-2024243548 A1 | 11/2024 |
| WO | WO-2025024465 A1 | 1/2025 |
| WO | WO-2025024672 A1 | 1/2025 |

OTHER PUBLICATIONS

Golden et al.: A portable automated multianalyte biosensor. 65(5):1078-1085 doi:10.1016/j.talanta.2004.03.072 (Abstract) (2005).

Kocheril et al.: Amplification-free nucleic acid detection with a fluorescence-based waveguide biosensor. Front. Sens. 3:948466, pp. 1-11. doi:10.3389/fsens.2022.948466 (2022).

Liu et al.: An array fluorescent biosensor based on planar waveguide for multi-analyte determination in water samples. Sensors and Actuators B: Chemical. 240:107-113 (Abstract) (2017a).

Liu et al.: Integrated optical waveguide-based fluorescent immunosensor for fast and sensitive detection of microcystin-LR in lakes: Optimization and Analysis. Sci Rep. 7(1):3655, pp. 1-9. doi:10.1038/s41598-017-03939-8 (2017b).

Taitt et al.: Evanescent wave fluorescence biosensors: Advances of the last decade. Biosens Bioelectron. 76:103-112 doi:10.1016/j.bios.2015.07.040 (2016).

Kramer et al., Spanning binding sites on allosteric proteins with polymer-linked ligand dimers. Nature. 395(6703):710-713 (1998).

Co-pending U.S. Appl. No. 18/680,203, inventors Guo; Minghao et al., filed on May 31, 2024.

Co-pending U.S. Appl. No. 18/781,420, inventors Arslan; Sinan et al., filed on Jul. 23, 2024.

Co-pending U.S. Appl. No. 18/815,564, inventors Arslan; Sinan et al., filed on Aug. 26, 2024.

Pitino, Emanuele et al. STAMP: Single-Cell Transcriptomics Analysis and Multimodal Profiling through Imaging. bioRxiv preprint doi: https://doi.org/10.1101/2024.10.03.616013 pp. 1-29 (2024).

\* cited by examiner

5-Propargylamino-dUTP, 5-Propargyl-dUTP 5-(3-Aminoallyl)-2'-deoxyuridine-5'-triphosphate FIG. 12A
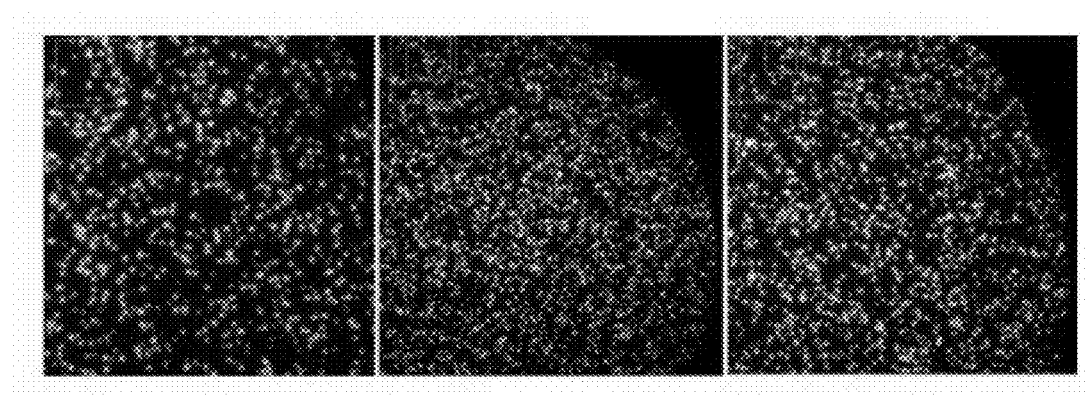
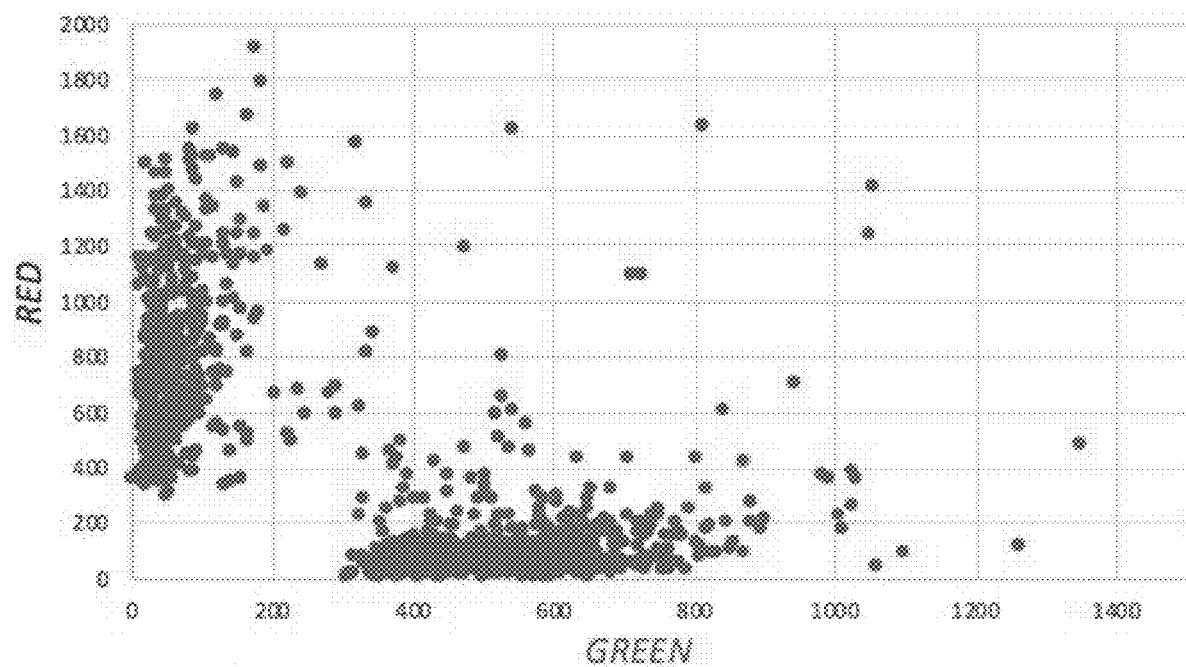
FIG. 12B

POLYMERASE-NUCLEOTIDE CONJUGATES FOR SEQUENCING BY TRAPPING

CROSS-REFERENCE

This application is a continuation of PCT/US20/34102 filed on May 21, 2020, and claims the benefit of U.S. Provisional Application No. 62/852,876, filed on May 24, 2019, both of which applications are incorporated herein by reference.

BACKGROUND OF THE INVENTION

The present disclosure addresses the technical problem of determining a nucleic acid sequence, e.g., a deoxyribonucleic acid (DNA) sequence of a template DNA in a highly parallelized format. Current methods of DNA sequencing couple a DNA base specific signal (e.g., incorporation of deoxyadenosine (dA), deoxycytidine (dC), (deoxyguanosine (dG), or deoxythymidine (dT)) to a readout method (typically fluorescence). As an example, in many of the methods currently in use, a DNA nucleotide is conjugated to a fluorescent dye having a specific fluorescence emission wavelength, with each of the bases conjugated to a dye having a different fluorescence emission wavelength. Following incorporation of the fluorescent nucleotide, a laser or other light source is used to excite the dye, and a camera or other detection system can be used to determine the wavelength (i.e., color) of the dye's fluorescence emission and therefore the type of base incorporated.

Other approaches to base-pair detection during sequencing reactions have used enzyme-linked nucleotides for Sequencing by Synthesis (SBS) and gene synthesis schemes. In these schemes, the attached nucleotide is catalytically incorporated into the growing DNA strand. These SBS methods require a different conjugation chemistry for attaching the enzyme to the nucleotide so that the incorporated product does not retain a covalently attached enzyme (e.g., using a phosphate-linked approach). To date, these approaches have not yet been adopted for commercial nucleic acid sequencing applications, and there remains a need for improved and simplified base-pairing detection schemes.

SUMMARY OF THE INVENTION

Disclosed herein are nucleic acid binding compositions comprising a nucleic acid binding moiety and a base-pairing moiety, wherein the base-pairing moiety is connected to the nucleic acid binding moiety via a linker, and wherein the linker has a length effective to allow the base-pairing moiety to pair with a complementary nucleotide in a primed polynucleotide while precluding incorporation of the base-pairing moiety into a 3' end of the polynucleotide. In some embodiments, the base-pairing moiety comprises a nucleotide or nucleotide analog. In some embodiments, the nucleic acid binding moiety comprises an enzyme, or a catalytic domain or fragment thereof. In some embodiments, the nucleic acid binding moiety comprises a polymerase, or a catalytic domain or fragment thereof. In some embodiments, the nucleic acid binding moiety comprises a reverse transcriptase, or a catalytic domain or fragment thereof. In some embodiments, the linker comprises a nucleic acid, a peptide, or a polymer. In some embodiments, the linker comprises PEG, and wherein the PEG linker has an average molecular weight of between about 5K Daltons and about 20K Daltons. In some embodiments, the nucleotide or nucleotide analog is conjugated to the linker through the 5' end of the nucleotide or nucleotide analog. In some embodiments, at least one nucleotide or nucleotide analog comprises a deoxyribonucleotide, a ribonucleotide, a deoxyribonucleoside, or a ribonucleoside. In some embodiments, at least one nucleotide or nucleotide analog is a nucleotide that has been modified to inhibit elongation during a polymerase reaction or a sequencing reaction. In some embodiments, at least one nucleotide or nucleotide analog is a nucleotide that lacks a 3' hydroxyl group. In some embodiments, at least one nucleotide or nucleotide analog is a nucleotide that has been modified to contain a blocking group at the 3' position. In some embodiments, the nucleic acid binding composition further comprises one or more detectable labels. In some embodiments, the nucleic acid binding composition further comprises one or more fluorescent labels. In some embodiments, the nucleic acid binding moiety is incapable of catalyzing an extension of an elongating nucleic acid chain. In some embodiments, the nucleic acid binding moiety lacks a salt, substrate, or cofactor that is necessary for catalyzing the extension of the elongating nucleic acid chain. In some embodiments, the nucleic acid binding moiety comprises a catalytically inactive polymerase, reverse transcriptase, or domain or fragment thereof. In some embodiments, Also disclosed herein are nucleic acid binding compositions comprising a mixture of at least one nucleic acid binding moiety and at least four different nucleotides or nucleotide analogs, wherein each nucleic acid binding moiety is tethered to one of the at least four different nucleotides or nucleotide analogs via a linker, and wherein a length of the linker is different for different nucleotides or nucleotide analogs. In some embodiments, one of the four different nucleotides or nucleotide analogs comprises a ribonucleotide or a ribonucleoside. In some embodiments, the length of the linker is between 1 nm and 1,000 nm.

Disclosed herein are nucleic acid binding compositions comprising a nucleic acid binding moiety and a nucleotide or nucleotide analog, wherein the nucleotide or nucleotide analog is connected to the nucleic acid binding moiety via a linker, and wherein the linker has a length effective to allow the nucleotide or nucleotide analog to pair with a complementary nucleotide while precluding incorporation of the nucleotide or nucleotide analog into the 3' end of a polynucleotide. Also disclosed are nucleic acid binding compositions comprising a mixture of at least one nucleic acid binding moiety and at least four different nucleotides or nucleotide analogs, wherein each nucleic acid binding moiety is tethered to one of the at least four different nucleotides or nucleotide analogs via a linker, and wherein the length of the linker is different for different nucleotide or nucleotide analog.

In some embodiments, the nucleic acid binding moiety comprises an enzyme, or a catalytic domain or fragment thereof. In some embodiments, the nucleic acid binding moiety comprises a polymerase, or a catalytic domain or fragment thereof. In some embodiments, the nucleic acid binding moiety comprises a reverse transcriptase, or a catalytic domain or fragment thereof. In some embodiments, the nucleic acid binding moiety comprises one or more of a Pol I polymerase, a Bsu polymerase, a Bst polymerase, a Pfu polymerase, a Taq polymerase, a Klenow fragment polymerase, a 9° N polymerase, or any catalytic domain, fragment, or variant thereof. In some embodiments, the nucleic acid binding moiety comprises one or more of an MMLV reverse transcriptase, an HIV class M reverse transcriptase, an HIV class O reverse transcriptase, an HBV reverse transcriptase, an HCV reverse transcriptase, an AMV reverse transcriptase, or any catalytic domain, fragment, or variant thereof. In some embodiments, the linker comprises a nucleic acid, a peptide, or a polymer. In some embodiments, the linker comprises polyethylene glycol, polypropylene glycol, polyvinyl acetate, polylactic acid, or polyglycolic acid. In some embodiments, the linker comprises PEG. In some embodiments, the linker comprises PEG, and wherein the PEG moiety has an average molecular weight of about 1K Da, about 2K Da, about 3K Da, about 4K Da, about 5K Da, about 10K Da, about 15K Da, or about 20K Da. In some embodiments, the linker comprises PEG, and wherein the PEG moiety has an average molecular weight of between about 5K Da and about 20K Da. In some embodiments, the nucleotide or nucleotide analog is conjugated to the linker through the 5' end of the nucleotide or nucleotide analog. In some embodiments, at least one nucleotide or nucleotide analog comprises a deoxyribonucleotide, a ribonucleotide, a deoxyribonucleoside, or a ribonucleoside. In some embodiments, one of the four different nucleotides or nucleotide analogs comprises a ribonucleotide or a ribonucleoside. In some embodiments, one of the four different nucleotides or nucleotide analogs comprises deoxyadenosine, and the length of the linker is between 1 and 1,000 nm. In some embodiments, one of the four different nucleotides or nucleotide analogs comprises deoxyguanosine, and the length of the linker is between 1 and 1,000 nm. In some embodiments, one of the four different nucleotides or nucleotide analogs comprises thymidine, and the length of the linker is between 1 and 1,000 nm. In some embodiments, one of the four different nucleotides or nucleotide analogs comprises deoxyuridine, and the length of the linker is between 1 and 1,000 nm. In some embodiments, one of the four different nucleotides or nucleotide analogs comprises deoxycytidine, and the length of the linker is between 1 and 1,000 nm. In some embodiments, one of the four different nucleotides or nucleotide analogs comprises adenosine, and the length of the linker is between 1 and 1,000 nm. In some embodiments, one of the four different nucleotides or nucleotide analogs comprises guanosine, and the length of the linker is between 1 and 1,000 nm. In some embodiments, one of the four different nucleotides or nucleotide analogs comprises 5-methyl-uridine, and the length of the linker is between 1 and 1,000 nm. In some embodiments, one of the four different nucleotides or nucleotide analogs comprises uridine, and the length of the linker is between 1 and 1,000 nm. In some embodiments, one of the four different nucleotides or nucleotide analogs comprises cytidine, and the length of the linker is between 1 and 1,000 nm. In some embodiments, at least one nucleotide or nucleotide analog is a nucleotide that has been modified to inhibit elongation during a polymerase reaction or a sequencing reaction. In some embodiments, at least one nucleotide or nucleotide analog is a nucleotide that lacks a 3' hydroxyl group. In some embodiments, at least one nucleotide or nucleotide analog is a nucleotide that has been modified to contain a blocking group at the 3' position. In some embodiments, at least nucleotide or nucleotide analog is a nucleotide that has been modified with a 3'-O-azido group, a 3'-0-azidomethyl group, a 3'-phosphorothioate group, a 3'-O-malonyl group, or a 3'-O-benzyl group. In some embodiments, at least one nucleotide or nucleotide analog is a nucleotide that has not been modified at the 3' position. In some embodiments, the nucleic acid binding moiety comprises one or more detectable labels. In some embodiments, the nucleic acid binding moiety comprises one or more fluorescent labels. In some embodiments, the nucleic acid binding moiety is unlabeled. In some embodiments, at least one nucleotide or nucleotide analog comprises one or more detectable labels. In some embodiments, at least one base-pairing comprises one or more fluorescent labels. In some embodiments, the nucleotide or nucleotide analog is unlabeled. In some embodiments, the linker comprises one or more detectable labels. In some embodiments, the linker comprises one or more fluorescent labels. In some embodiments, the linker is unlabeled. In some embodiments, the nucleic acid binding moiety is incapable of catalyzing an extension of an elongating nucleic acid chain. In some embodiments, the nucleic acid binding moiety lacks a salt, substrate, or cofactor that is necessary for catalyzing the extension of the elongating nucleic acid chain. In some embodiments, the nucleic acid binding moiety comprises a catalytically inactive polymerase, reverse transcriptase, or domain or fragment thereof. In some embodiments, the nucleic acid binding moiety comprises a catalytically inactive Pol I polymerase, Bsu polymerase, Bst polymerase, Pfu polymerase, Taq polymerase, Klenow fragment polymerase, 9° N polymerase, MMLV reverse transcriptase, HIV class M reverse transcriptase, HIV class O reverse transcriptase, HBV reverse transcriptase, HCV reverse transcriptase, AMV reverse transcriptase, or any domain, fragment, or variant thereof.

Also disclosed herein are methods of determining the sequence of a nucleic acid molecule comprising: a) contacting a double-stranded or partially double-stranded nucleic acid molecule comprising a template strand to be sequenced and a complementary strand to be elongated with one or more nucleic acid binding compositions according to any one of the embodiments described herein; and b) detecting binding of a nucleic acid binding composition to the nucleic acid molecule, thereby determining the presence of one of said one or more nucleic acid binding compositions on said nucleic acid molecule, and thereby determining an identity of a terminal nucleotide to be incorporated into said complementary strand of said nucleic acid molecule.

In some embodiments, the method further comprises incorporating said terminal nucleotide into said complementary strand, and repeating said contacting, detecting, and incorporating steps for one or more additional iterations, thereby determining the sequence of said template strand of said nucleic acid molecule. In some embodiments, said nucleic acid molecule is tethered to a solid support. In some embodiments, the solid support comprises a glass or polymer substrate, at least one hydrophilic polymer coating layer, and a plurality of oligonucleotide molecules attached to at least one hydrophilic polymer coating layer. In some embodiments, at least one hydrophilic polymer coating layer comprises PEG. In some embodiments, at least one hydrophilic polymer layer comprises a branched hydrophilic polymer having at least 8 branches. In some embodiments, the plurality of oligonucleotide molecules is present at a surface density of at least 500,000 molecules/$\mu m^2$. In some embodiments, said nucleic acid molecule has been clonally-amplified on a solid support. In some embodiments, the clonal amplification comprises the use of a polymerase chain reaction (PCR), multiple displacement amplification (MDA), transcription-mediated amplification (TMA), nucleic acid sequence-based amplification (NASBA), strand displacement amplification (SDA), real-time SDA, bridge amplification, isothermal bridge amplification, rolling circle amplification, circle-to-circle amplification, helicase-dependent amplification, recombinase-dependent amplification, single-stranded binding (SSB) protein-dependent amplification, or any combination thereof. In some embodiments, the one or more nucleic acid binding compositions are labeled with fluorophores and the detecting step comprises use of fluorescence imaging. In some embodiments, the fluorescence imaging comprises dual wavelength excitation/four wavelength emission fluorescence imaging. In some embodiments, four different nucleic acid binding compositions, each comprising a different nucleotide or nucleotide analog, are used to determine the identity of the terminal nucleotide, wherein the four different nucleic acid binding compositions are labeled with cyanine dye 3 (Cy3), cyanine dye 3.5 (Cy3.5), cyanine dye 5 (Cy5), and cyanine dye 5.5. (Cy5.5) respectively, and wherein the detecting step comprises simultaneous excitation at 532 nm and 633 nm and imaging of fluorescence emission at about 570 nm, 592 nm, 670 nm, and 702 nm respectively. In some embodiments, the fluorescence imaging comprises dual wavelength excitation/ dual wavelength emission fluorescence imaging. In some embodiments, four different nucleic acid binding compositions, each comprising a different nucleotide or nucleotide analog, are used to determine the identity of the terminal nucleotide, wherein one of the four different nucleic acid binding compositions is labeled with a first fluorophore, one is labeled with a second fluorophore, one is labeled with both the first and second fluorophore, and one is not labeled, and wherein the detecting step comprises simultaneous excitation at a first excitation wavelength and a second excitation wavelength and images are acquired at a first fluorescence emission wavelength and a second fluorescence emission wavelength. In some embodiments, the first fluorophore is Cy3, the second fluorophore is Cy5, the first excitation wavelength is 532 nm, the second excitation wavelength is 633 nm, the first fluorescence emission wavelength is about 570 nm, and the second fluorescence emission wavelength is about 670 nm. In some embodiments, a sequencing reaction cycle comprising the contacting, detecting, and incorporating steps is performed in less than 30 minutes. In some embodiments, a sequencing reaction cycle comprising the contacting, detecting, and incorporating steps is performed in less than 20 minutes. In some embodiments, a sequencing reaction cycle comprising the contacting, detecting, and incorporating steps is performed in less than 10 minutes. In some embodiments, an average Q-score for base calling accuracy over a sequencing run is greater than or equal to 30. In some embodiments, an average Q-score for base calling accuracy over a sequencing run is greater than or equal to 40. In some embodiments, at least 90% of the terminal nucleotides identified have a Q-score of greater than 30. In some embodiments, at least 95% of the terminal nucleotides identified have a Q-score of greater than 30. In some embodiments, at least 9% of the terminal nucleotides identified have a Q-score of greater than 40.

Disclosed herein are reagents comprising one or more nucleic acid binding compositions according to any of the embodiments described herein and a buffer. In some embodiments, said reagent comprises 1, 2, 3, 4, or more nucleic acid binding compositions, wherein each nucleic acid binding composition comprises a single type of nucleotide or nucleotide analog, and wherein said nucleotide or nucleotide analog comprises a nucleotide, nucleotide analog, nucleoside, or nucleoside analog. In some embodiments, said reagent comprises 1, 2, 3, 4, or more nucleic acid binding compositions, wherein each nucleic acid binding composition comprises a single type of nucleotide or nucleotide analog, and wherein said nucleotide or nucleotide analog may respectively correspond to one or more from the group consisting of adenosine triphosphate (ATP), adenosine diphosphate (ADP), adenosine monophosphate (AMP), deoxyadenosine triphosphate (dATP), deoxyadenosine diphosphate (dADP), and deoxyadenosine monophosphate (dAMP); one or more from the group consisting of thymidine triphosphate (TTP), thymidine diphosphate (TDP), thymidine monophosphate (TMP), deoxythymidine triphosphate (dTTP), deoxythymidine diphosphate (dTDP), deoxythymidine monophosphate (dTMP), uridine triphosphate (UTP), uridine diphosphate (UDP), usridine monophosphate (UMP), deoxyuridine triphosphate (dUTP), deoxyuridine diphosphate (dUDP), and deoxyuridine monophosphate (dUMP); one or more from the group consisting of cytidine triphosphate (CTP), cytidine diphosphate (CDP), cytidine monophosphate (CMP), deoxycytidine triphosphate (dCTP), deoxycytidine diphosphate (dCDP), and deoxycytidine monophosphate (dCMP); and one or more from the group consisting of guanosine triphosphate (GTP), guanidine diphosphate (GDP), guanosine monophosphate (GMP), deoxyguanosine triphosphate (dGTP), deoxyguanosine diphosphate (dGDP), and deoxyguanosine monophosphate (dGMP). In some embodiments, said reagent comprises 1, 2, 3, 4, or more nucleic acid binding compositions, wherein each nucleic acid binding composition comprises a single type of nucleotide or nucleotide analog, and wherein said nucleotide or nucleotide analog may respectively correspond to one or more from the group consisting of ATP, ADP, AMP, dATP, dADP, dAMP TTP, TDP, TMP, dTTP, dTDP, dTMP, UTP, UDP, UMP, dUTP, dUDP, dUMP, CTP, CDP, CMP, dCTP, dCDP, dCMP, GTP, GDP, GMP, dGTP, dGDP, and dGMP.

Disclosed herein are kits comprising the nucleic acid binding composition of any of the embodiments described herein and/or the reagent of any of the embodiments described herein; one or more buffers; and instructions for the use thereof.

Disclosed herein are systems for performing the method of any embodiment described herein, comprising a nucleic acid binding composition of any of the embodiments described herein and/or a reagent of any of the embodiments described herein, one or more buffers, and one or more nucleic acid molecules tethered to a solid support, wherein said system is configured to iteratively perform for the sequential contacting of said tethered nucleic acid molecules with said nucleic acid binding composition of any of the embodiments described herein and/or said reagent of any of the embodiments described herein; and for the detection of binding of the nucleic acid binding compositions to the one or more nucleic acid molecules.

INCORPORATION BY REFERENCE

All publications, patents, and patent applications mentioned in this specification are herein incorporated by reference in their entirety to the same extent as if each individual publication, patent, or patent application was specifically and individually indicated to be incorporated by reference in its entirety. In the event of a conflict between a term herein and a term in an incorporated reference, the term herein controls.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 4A: NHS-PEG (10K)-NHS tether. FIG. 4B: HS-PEG (10K)-COOH tether. FIG. 4C: $H_2N$-PEG (10K)-COOH tether. FIG. 4D: HS-PEG (10K)-$NH_2$ tether. FIG. 4E: COOH-PEG (10K)-$NH_2$ tether. FIG. 4F: NHS ester—$NH_2$ coupling of dNTPs.

FIGS. 12A-B provide a non-limiting example of data illustrating sequencing reactions using polynucleotides tethered to a substrate surface, without performing the cleavage of the linkage between the dNTP moiety and the polymerase (dTTP, red and dGTP, green). FIG. 12A: image data illustrating sequencing reactions performed using conjugates comprising a dTTP moiety (red) and a dGTP moiety (green) as the tethered nucleotide. FIG. 12B: scatter plot of two-channel fluorescence intensity data derived from images such as those shown in FIG. 12A.

DETAILED DESCRIPTION OF THE INVENTION

Figure 1:
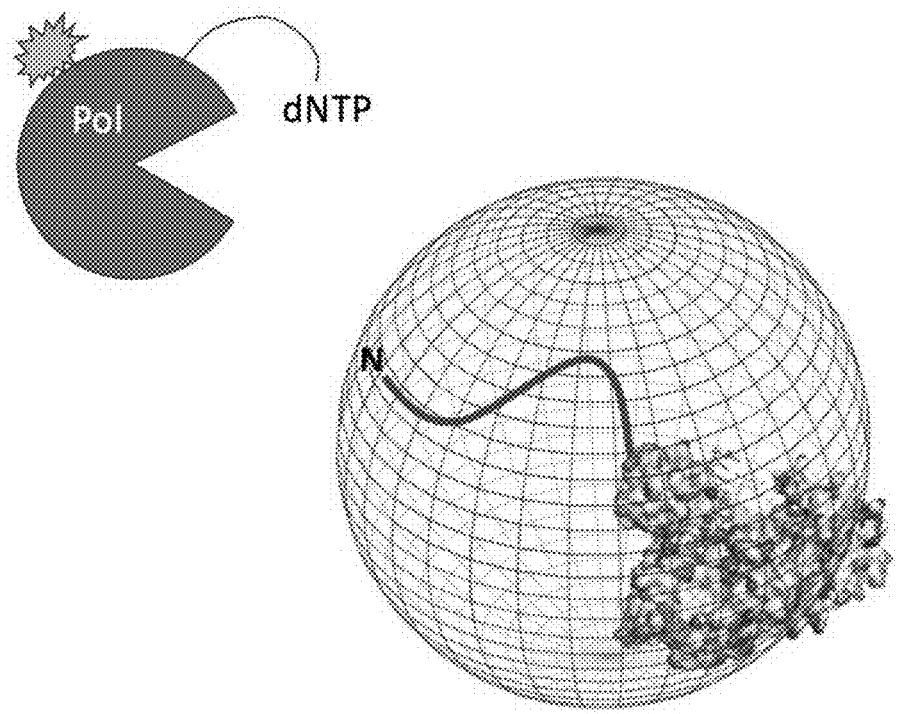
FIG. 1 provides a schematic illustration of the structure of a nucleotide-tethered polymerase and the volume surrounding the polymerase that may be sampled by the tethered nucleotide.

This disclosure describes an improved method to optically determine the sequence of a target DNA molecule (or other nucleic acid) using a non-catalytic reporter capable of discerning nucleic acid sequence information without chemically altering the nucleic acid. In this "sequencing by trapping" (SBT) approach, a DNA binding moiety capable of recognizing the site of elongation of a nucleic acid primer, such as a polymerase or the nucleic acid binding elements of a polymerase, is conjugated to a base-pairing moiety (e.g., a nucleotide) via a PEG (or other suitable) linker. In some instances, the nucleic acid binding moiety or, using the example of a polymerase enzyme, the enzyme, may also be conjugated to one or more fluorescent dye molecules or other labels or tags. In some instances, this conjugation may occur via an orthogonal chemistry compared to that used to attach the enzyme to the nucleotide.

Enzyme-linked nucleotides may then be prepared in parallel fashion so that each DNA base is conjugated to a polymerase labeled with a different emission wavelength dye. These conjugates may then be mixed and reacted with the template DNA in question under conditions that render the polymerase or nucleic acid binding moiety catalytically deficient. As used herein, the term "catalytically deficient" refers to any condition under which a polymerase or nucleic acid binding moiety is incapable of efficiently catalyzing modifications of DNA, nucleotides, or other elements of a nucleoprotein complex or a sequencing reaction. In some instances, the conditions used to render a polymerase or nucleic acid binding moiety catalytically deficient may include, but are not limited to: use of an enzyme containing a point mutation that allows nucleotide binding but blocks catalysis, use of a non-incorporable nucleotide or other base-pairing moiety, reaction conditions comprising the use of a non-catalytic divalent metal cofactor or removing a required catalytic metal cofactor, reaction conditions comprising the use of a primer lacking a free 3'-OH, or any combination thereof.

The use of enzyme-linked substrates specifically for binding to create a detectable signal provides a novel approach to the problem of detecting and resolving the identity of the N+1 residue of the template nucleic acid sequence (i.e., the nucleotide residue adjacent to the free 3'-OH end of a complementary primer extension strand of N bases in length) during a sequencing reaction. The present disclosure thus describes novel compositions, reagents, and methods whereby an enzyme-linked base-pairing moiety can be used to detect which base is present at the N+1 position without modifying the DNA or other nucleic acid sequence that is being probed. The sequencing schemes enabled by the compositions and methods described herein may also eliminate the need for multiple rounds of imaging to achieve 4 base determination. Reducing the imaging time required for 4 base determination may decrease overall sequencing cycle time and provide for higher sequencing throughput.

Furthermore, the cost of the enzyme linked nucleotide or nucleotide analogs described herein are lower than that for the labeled nucleotides or nucleotide analogs used in sequencing by synthesis methods. The sequencing methods using the enzyme linked nucleotide or nucleotide analogs described herein therefore are faster and more cost-efficient and accurate than other sequencing methods such as the sequencing by synthesis methods.

Various aspects of the disclosed compositions, methods, systems, and kits described herein may be applied to any of the particular nucleic acid sequencing applications set forth below, or for any other types of nucleic acid analysis applications known to those of skill in the art. It shall be understood that different aspects of the disclosed compositions, methods, systems, and kits can be appreciated individually, collectively, or in combination with each other.

Definitions: Unless otherwise defined, all of the technical terms used herein have the same meaning as commonly understood by one of ordinary skill in the art in the field to which this disclosure belongs.

As used in this specification and the appended claims, the singular forms "a", "an", and "the" include plural references unless the context clearly dictates otherwise. Any reference to "or" herein is intended to encompass "and/or" unless otherwise stated.

As used herein, the term 'about' a number refers to that number plus or minus 10% of that number. The term 'about' when used in the context of a range refers to that range minus 10% of its lowest value and plus 10% of its greatest value.

Principle of the method: Without intending to be bound by any particular theory, it is possible to describe the method disclosed herein as follows. DNA sequencing reactions (or other nucleic acid sequencing reactions) can be performed by reacting a pool of the enzyme-nucleotide conjugates with DNA molecules where the N+1 base is unknown. The reaction conditions occur in an environment that disfavors DNA-Enzyme interactions unless the correct nucleotide is bound. This process can, for example, be described as using conditions that increase the Enzyme-DNA $K_d$, thereby creating an equilibrium that strongly favors the unbound state but allowing the enzyme to rapidly and transiently associate and dissociate from the DNA. In this situation, binding of the enzyme to the DNA in the presence of an incorrect nucleotide would lead to rapid dissociation of the enzyme-DNA complex, while binding of the enzyme to the DNA in the presence of the correct nucleotide leads to conversion of the complex into a more stable state (for some enzymes this will be referred to as the "closed" state) which enables further probing and/or detection of the enzyme-DNA-nucleotide complex. Appropriate conditions may be obtained, for example, by altering buffer conditions to disfavor enzyme-DNA binding interactions, by altering the structure and/or sequence of the polymerase (or other nucleic acid binding moiety) to disfavor binding interactions with DNA, by choosing substrates (also referred to herein as base-pairing moieties) such as nucleotides, nucleosides, or analogues thereof which disfavor enzyme-DNA binding interactions, or by other means as are known in the art for the modulation and/or reduction of enzyme-DNA binding interactions.

The use of linked nucleotides facilitates the identification of the N+1 nucleotide by increasing the effective local concentration of a particular nucleotide. While the enzyme is transiently bound to the nucleic acid and before dissociation, the linked nucleotide can be sampled by the enzyme at the active site. Because of the linkage between the enzyme and the nucleotide, a bound enzyme preferably samples the nucleotide to which it is linked. Therefore, using the example given above, an enzyme tethered or linked to the incorrect nucleotide would primarily be present in the unbound state, while an enzyme linked or tethered to the correct nucleotide would primarily be present in a bound complex. Specific labeling of each nucleotide, of the linker attached to each nucleotide, of the polymerase or other nucleic acid binding moiety attached to each nucleotide, and/or of other moieties attached to each nucleotide with a detectable label, e.g., a fluorophore, allows identification of each specific nucleotide-DNA-polymerase, nucleotide-DNA-nucleic acid binding moiety, or other nucleotide-DNA conjugates in such a manner as to identify the nucleotide present in each enzyme-DNA complex. In some instances, the nucleic acid binding moiety comprises one or more detectable labels. In some instances, the nucleic acid binding moiety comprises one or more fluorescent labels. In some instances, the nucleic acid binding moiety is unlabeled. In some instances, the base-pairing moiety comprises one or more detectable labels. In some instances, the base-pairing comprises one or more fluorescent labels. In some instances, the base-pairing moiety is unlabeled. In some instances, the linker comprises one or more detectable labels. In some instances, the linker comprises one or more fluorescent labels. In some instances, the linker is unlabeled.

Thus, labeling of enzyme-nucleotide conjugates, e.g., with a suitable selection of fluorophores, allows for 4 base determination from a single fluorescence scanning cycle. In some embodiments, 1, 2, 3, 4, or more nucleotide types (e.g., ATP, dATP, TTP, dTTP, CTP, dCTP, GTP, or dGTP) are tethered to 1, 2, 3, 4, or more different polymerases, wherein each nucleotide type is tethered to a different polymerase, and each polymerase has a different exogenous label or a detectable feature to differentiate it from the other polymerases and thus enable its identification. All tethered nucleotide types can be added together to a sequencing reaction mixture, with base-pairing of the correct nucleotide leading to the formation of a closed-complex comprising a tethered nucleotide-polymerase-primer sequence—template nucleic acid; and the closed-complex is monitored to identify the polymerase, thereby identifying the next correct nucleotide to which the polymerase is tethered. In some instances, the tethering of the nucleotide to the polymerase may occur at the gamma phosphate of the nucleotide through a multi-phosphate group and a linker molecule. Such gamma-phosphate linking methods (where a fluorophore is attached to the gamma phosphate linker) are known in the art. Optionally, different nucleotide types can be identified by using distinguishable exogenous labels on the different enzyme-nucleotide conjugates. Optionally, the distinguishable exogenous labels are attached to the gamma phosphate position of each nucleotide.

Again, if the sampled nucleotide is the correct cognate for the template DNA, a kinetically favored conformation is adopted (often referred to as the "closed" state). In this state the bound enzyme-DNA-nucleotide complex is poised for catalysis. However, catalysis can be blocked, e.g., by mutation of the catalytic residues of the enzyme active site, or by manipulation of the buffer conditions used for the binding reaction, or by any other method as disclosed herein or known in the art. Prevention of catalysis prevents the extension of the primer chain and provides an opportunity to identify, locate, probe, or otherwise interrogate the bound enzyme-DNA-nucleotide complex.

If the sampled nucleotide is the incorrect nucleotide, the polymerase or nucleic acid binding moiety fails to adopt the "closed" conformation or fails to stabilize the complex and the transient enzyme-DNA complex dissociates. Where template DNA or DNA-primer complexes are localized, such as by attachment to a surface or by aggregation in space or in solution, applying a detection method as described elsewhere herein may then provide discrimination between bound and unbound enzyme, nucleotide, or DNA binding moiety, as stably bound enzyme-DNA-nucleotide complexes (i.e., those complexes that include the correct nucleotide at the N+1 position) will be readily detectable as foci of the detection signal (for example, fluorescence, where one or more components of the complex is fluorescently labeled). Unbound enzyme, nucleotide, or other elements of unformed complexes will be less readily detectable as the lack of binding may leave them free in solution, where they will be susceptible to removal by washing and/or difficult to detect due to the diffuse nature of the components suspended in solution.

As noted above, the use of enzyme-linked nucleotides facilitates the identification of the N+1 nucleotide by increasing the effective local concentration of a particular nucleotide. Without intending to be bound by any particular theory, in some instances the concentration of the correct nucleotide may be modeled as equimolar with the polymerase within a spheroid having a primary radius defined by the length of the fully extended linker (see, for example, FIG. 1). Alternatively, in some instances the concentration of the correct nucleotide may be modeled as at least equimolar with the polymerase within a spheroid having a primary radius defined by the length of the fully extended linker. In a further alternative, the concentration of the correct nucleotide may be modeled as at least equimolar with the polymerase within a spheroid with a primary radius defined by the persistence length of the linker. The persistence length of the linker may be determined in free solution, in water solution, in air, in one or more sequencing, imaging, or detection solutions or buffers, in vacuo, in silico, or by any method as is known in the art for determining equilibrium polymer lengths under conditions relevant to the preparation and use of sequencing and/or detection solutions as disclosed herein. In some alternatives, the concentration of the correct nucleotide may be modeled as at least equimolar with the polymerase within a spheroid centered on the center of rotation of the polymerase molecule. In some alternatives, the concentration of the correct nucleotide may be modeled as at least equimolar with the polymerase within a spheroid centered on the locus of attachment of the linker on the polymerase molecule. For example, in conjugates where a single nucleotide is linked via a linker to a polymerase, the absolute concentration of nucleotide in the reaction is equimolar to the concentration of protein. The relative concentration of nucleotide to that of the enzyme to which it is coupled is defined with respect to the volume of a sphere, where the radius of the sphere is the length of the linker and will correspond to a concentration of at least one molecule of nucleotide per spherical volume. Regardless of the method used to model or define the relevant concentrations of polymerase and nucleotide, the result of the tethering is that a physiologically relevant concentration of a specific nucleotide molecule to a specific enzyme molecule is achieved at a total concentration of nucleotide that is lower than what would be required using untethered nucleotides in free solution. Further, the tethering allows control over which nucleotide is attached to which polymerase, and thus by differentially labeling any component of the nucleotide-polymerase construct it is possible to discriminate between polymerase molecules tethered to each individual nucleotide.

Nucleic acid binding compositions: A nucleic acid binding composition can include a nucleic acid binding moiety (e.g., a polymerase) and a base-pairing moiety (e.g., a nucleotide or nucleotide analog), wherein the base-pairing moiety is connected to the nucleic acid binding moiety via a linker, and wherein the linker has a length effective to allow the base-pairing moiety, e.g., the nucleotide or nucleotide analog, to pair with a complementary nucleotide while precluding incorporation of the nucleotide or nucleotide analog into the 3' end of a polynucleotide.

In some instances, the nucleic acid binding moiety may comprise a polymerase, a nucleic acid binding domain or sub-domain of a polymerase, a nucleic acid binding protein, a nucleic acid binding domain or sub-domain of a nucleic acid binding protein, or any combination thereof.

In some instances, the nucleic acid binding composition may comprise a nucleic acid binding moiety (e.g., a polymerase) and one or more base-pairing moieties (e.g., nucleotides or nucleotide analogs). In some instances, the nucleic acid binding composition may comprise 1, 2, 3, 4, 5, 6, 7, 8, 9, 10, or more than 10 base-pairing moieties tethered to a single nucleic acid binding moiety.

The nucleic acid binding composition can also include a mixture of at least one nucleic acid binding moiety and one, two, three, four, or more than four different nucleotides or nucleotide analogs, i.e., where the one or more nucleotides or nucleotide analogs tethered to any given nucleic acid binding moiety are the same, but where the mixture comprises nucleic acid binding moieties tethered to 1, 2, 3, 4, or more than 4 different nucleotides or nucleotide analogs. In the composition, the nucleic acid binding moiety is tethered to one of the four different nucleotides or nucleotide analogs via a linker. In some instances, the length of the linker is different for different nucleotides or nucleotide analogs. In some instances, the nucleic acid binding moiety for the different nucleotides or nucleotide analogs can be the same or different.

Nucleotides, nucleotide analogs and other base-pairing moieties: Examples of nucleotides or other base-pairing moieties that may be conjugated to the enzyme-complex include, but are not limited to: deoxynucleoside triphosphates (dNTPs), deoxynucleoside diphosphates (dNDPs), deoxynucleoside monophosphates (dNMPs), dideoxynucleoside triphosphates (ddNTPs), dideoxynucleoside diphosphates (ddNDPs), dideoxynucleoside monophosphates (ddNMPs), ribonucleoside triphosphates (rNTPs), ribonucleoside diphosphates (rNDPs), ribonucleoside monophosphates (rNMPs), non-hydrolyzable nucleotide analogs modified between the 1st and 2nd phosphosphate, nucleotide or nucleotide analogs having 4, 5, 6, 7, or 8 phosphate moieties, nucleotides containing 2' or 3' modifications, and/or nucleotides including base modifications. It is contemplated that any nucleotide, nucleoside, nucleotide analog, or nucleoside analog that can base-pair with the templating base and provide discrimination between the 4 bases may be suitable for use in the compositions and methods disclosed herein. In some embodiments, one nucleotide may be attached to a given linker or to a given nucleic acid binding moiety—base-pairing moiety conjugate. In some embodiments, more than one nucleotide may be attached to a given linker or to a given nucleic acid binding moiety—base-pairing moiety conjugate. In some embodiments, 2, 3, 4, 5, 6, 7, 8, 9, 10 or more nucleotides may be attached to a given linker or to a given nucleic acid binding moiety—base-pairing moiety conjugate. In some embodiments, the number of nucleotides present on a given linker or conjugate may vary within a population of polymerase-linker-nucleotide combinations. In some embodiments, all of the nucleotides present on a given linker or conjugate are identical. In some embodiments, all of the nucleotides present on a given linker or conjugate are not identical.

In some instances, the ribonucleotides or ribonucleotide analogs may work better than the counterpart deoxynucleotides and deoxynucleotide analogs when they are linked to enzymes and used in the sequencing by trapping methods described herein. In some instances, the nucleotide or nucleotide analogs are ribonucleotides or ribonucleotide analogs having 2, 3, 4, 5, or 6 phosphates, wherein the linker is attached to the nucleotide through the phosphate moiety.

Figure 2:
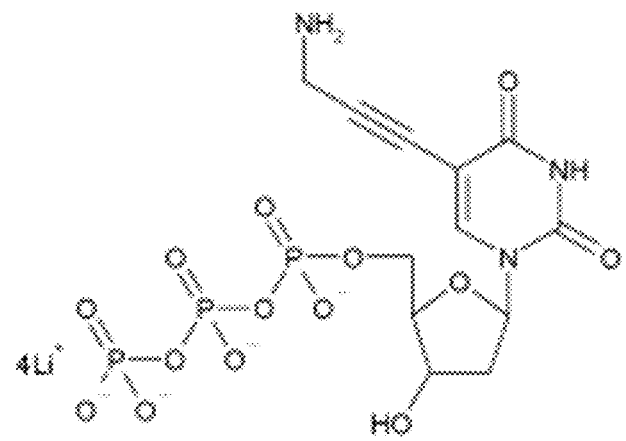
FIG. 2 provides non-limiting examples of amine-containing deoxynucleoside triphosphate (dNTP) structures.
Figure 2:
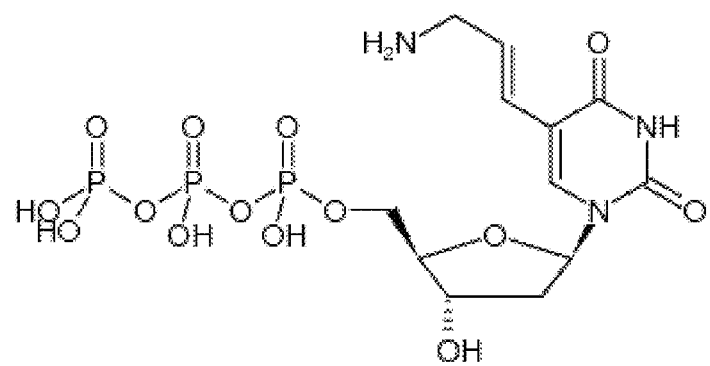

Linkers: In some embodiments, the present disclosure contemplates reagents comprising a polymerase or other nucleic acid binding moiety, attached to one or more linker(s) that connect the polymerase or other nucleic acid binding moiety to one or more base-pairing moieties, e.g., a modified nucleotide, which may in some further embodiments be incorporated into a nucleic acid-protein-nucleotide complex, and which may optionally be incorporated into a growing nucleic acid chain during a synthesis or elongation reaction. Conjugation of nucleotides or other base-pairing moieties to linkers may be achieved by any means known in the art of chemical conjugation methods. For example, nucleotides containing base modifications that add a free amine group are especially considered for use in conjugation to linkers as described herein. Primary amines, for example, may be linked to the base in such a manner that they can be reacted with heterobifunctional polyethylene glycol (PEG) linkers to create a nucleotide containing a variable length PEG linker that will still bind properly to the enzyme active site. Examples of such amine-containing nucleotides include 5-propargylamino-dNTPs, 5-propargylamino-NTPs, amino allyl-dNTPs, and amino allyl-NTPs (with exemplary amine-containing dNTP structures as shown in FIG. 2).

Figure 3:
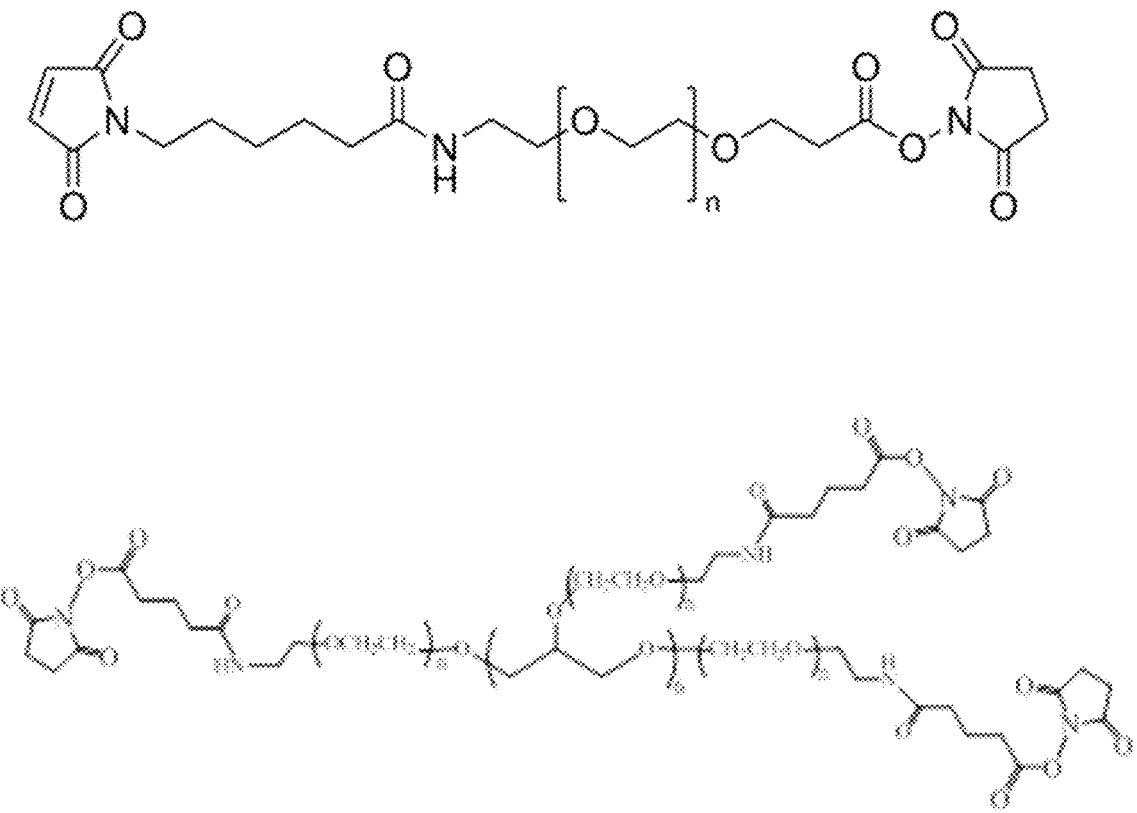
FIG. 3 provides a non-limiting example of the structure of a linear (top) and a branched (bottom) polyethylene (PEG) linker.
Figure 4A:
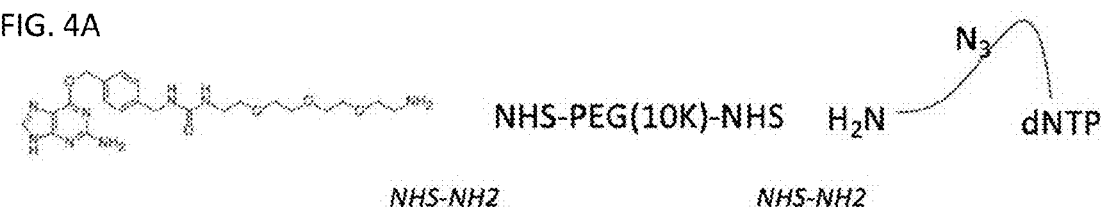
FIGS. 4A-F provide non-limiting examples of moieties which may be used to construct and/or attach linkers and linker-nucleotide combinations, each comprising a representative nucleotide (left), optionally a tether (center) and optionally a linker (right) (to polymerases or to protein linker components).
Figure 4B:
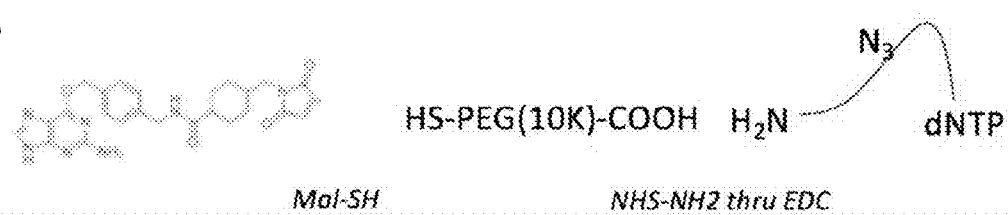
Figure 4C:
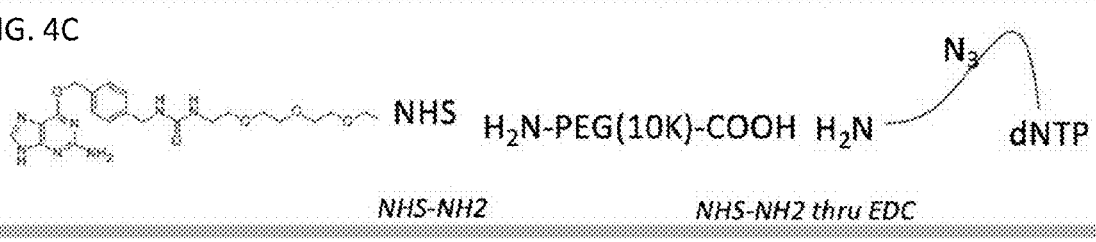
Figure 4D:
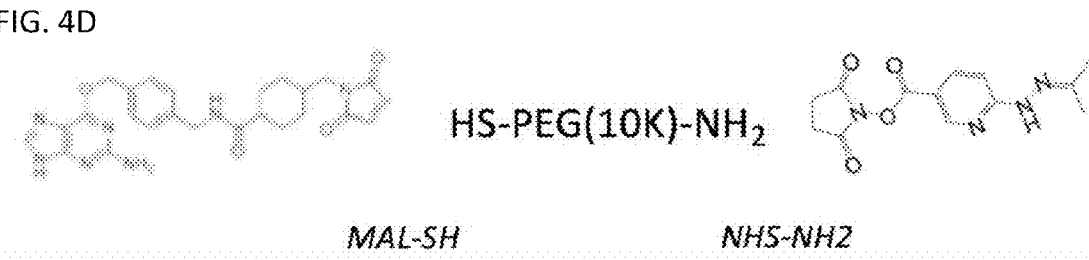
Figure 4E:
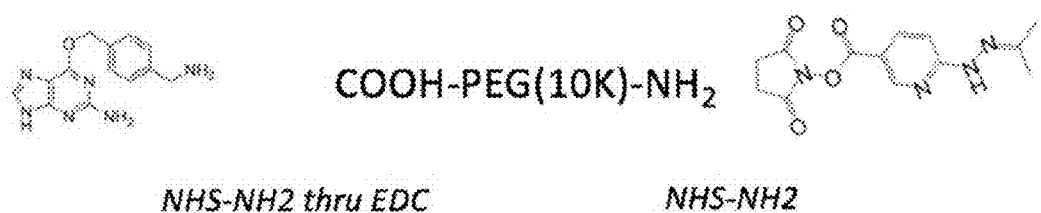
Figure 4F:
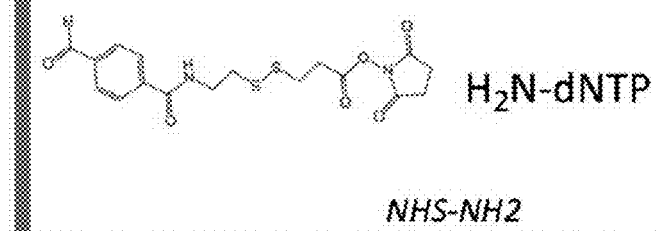

It is expressly contemplated that other linkers as known in the art and as disclosed herein may be used to generate the reagents of the present disclosure, and that alternative conjugation chemistries as known in the art and as disclosed herein may also be used to generate the reagents of the present disclosure. In an exemplary embodiment, amine-containing nucleotides are considered to be especially suitable for conjugation with PEG-based linkers. A number of suitable PEG linkers are known in the art and are commercially available. Suitable PEG linkers may vary in length, for example, from 1-1000, from 1-500, from 1-11, from 1-100, from 1-50, or from 1-10 subunits. In some embodiments, a PEG linker comprises less than 100 subunits. In some embodiments, a PEG linker comprises more than 100 subunits. In some embodiments, a PEG linker comprises more than 500 subunits. In some embodiments, a PEG linker comprises more than 1000 subunits. An non-limiting example of the structure of a linear PEG linker is shown in FIG. 3 (upper), where n=1-100. A non-limiting example of a branched PEG linker is shown in FIG. 3 (lower). In some instances, a suitable PEG linker (or a branch thereof) may comprise at least 10 subunits, at least 20 subunits, at least 30 subunits, at least 40 subunits, at least 50 subunits, at least 60 subunits, at least 70 subunits, at least 80 subunits, at least 90 subunits, at least 100 subunits, at least 200 subunits, at least 300 subunits, at least 400 subunits, at least 500 subunits, at least 600 subunits, at least 700 subunits, at least 800 subunits, at least 900 subunits, or at least 1,000 subunits. In some instances, a suitable PEG linker (or a branch thereof) may comprise at most 1,000 subunits, at most 900 subunits, at most 800 subunits, at most 700 subunits, at most 600 subunits, at most 500 subunits, at most 400 subunits, at most 300 subunits, at most 200 subunits, at most 100 subunits, at most 90 subunits, at most 80 subunits, at most 70 subunits, at most 60 subunits, at most 50 subunits, at most 40 subunits, at most 30 subunits, at most 30 subunits, or at most 10 subunits. Any of the lower and upper values described in this paragraph may be combined to form a range included within the present disclosure, for example, in some instances a suitable PEG linker (or a branch thereof) may comprise from about 90 subunits to about 400 subunits. Those of skill in the art will recognize that a suitable PEG linker (or branch thereof) may have any value within this range, e.g., about 225 subunits.

In some embodiments, a PEG linker may have an apparent average molecular weight, as measured by mass spectrometry, by electrophoretic methods, by size exclusion chromatography, by reverse-phase chromatography, or by any other means as known in the art for the estimation or measurement of the molecular weight of a polymer. In some instances, the apparent average molecular weight of the PEG selected for conjugation may be less than about 1,000 Da, less than about 2,000 Da, less than about 3,000 Da, less than about 4,000 Da, less than about 5,000 Da, less than about 7,500 Da, less than about 10,000 Da, less than about 15,000 Da, less than about 20,000 Da, less than about 50,000 Da, less than about 100,000 Da, or less than about 200,000 Da. In some instances, the apparent average molecular weight of the PEG selected for conjugation may be more than about 1,000 Da, more than about 2,000 Da, more than about 3,000 Da, more than about 4,000 Da, more than about 5,000 Da, more than about 7,500 Da, more than about 10,000 Da, more than about 15,000 Da, more than about 20,000 Da, more than about 50,000 Da, more than about 100,000 Da, or more than about 200,000 Da. Any of the lower and upper values described in this paragraph may be combined to form a range included within the present disclosure, for example, in some instances the apparent average molecular weight of the PEG selected for conjugation may range from about 2,000 Da to about 20,000 Da. Those of skill in the art will recognize that a suitable PEG linker may have any apparent average molecular weight within this range, e.g., about 2,600.

In some instances, non-PEG linkers may be utilized, as will be discussed in more detail below. Examples of other suitable linkers may include, but are not limited to, poly-T and poly-A oligonucleotide strands (e.g., ranging from about 1 base to about 1,000 bases in length), peptide linkers (e.g., poly-glycine or poly-alanine ranging from about 1 residue to about 1,000 residues in length), or carbon-chain linkers (e.g., C6, C12, C18, C24, etc.).

In some exemplary embodiments, the heterobifunctional linker may contain an N-hydroxysuccinimide ester (NHS) group. In some exemplary embodiments, the heterobifunctional linker may contain a maleimide group. In some exemplary embodiments, the heterobifunctional linker may contain an NHS group and a maleimide group. The NHS group of a linker may then react with a primary amine on a nucleotide or other base-pairing moiety, thereby creating a covalent attachment without modifying or destroying the maleimide group. Such a functionalized nucleotide may then be covalently attached to the enzyme by reaction of the maleimide group with a cysteine residue of the enzyme.

Examples of suitable conjugation chemistries for attaching nucleotides or other base-pairing moieties to tethers or linkers, and linkers to proteins or other nucleic acid binding moieties are illustrated in FIGS. 4A-F. Connection of the nucleotide can be achieved by the formation of a disulfide (forming a readily cleavable connection), formation of an amide, formation of an ester, protein-ligand linkage (e.g., biotin-streptavidin linkage), by alkylation (e.g., using a substituted iodoacetamide reagent) or forming adducts using aldehydes and amines or hydrazines. Numerous conjugation chemistries can be found in Hermanson, Bioconjugation Techniques, Academic Press, New York (May 2, 2008), which is incorporated herein by reference in its entirety.

Figure 5:
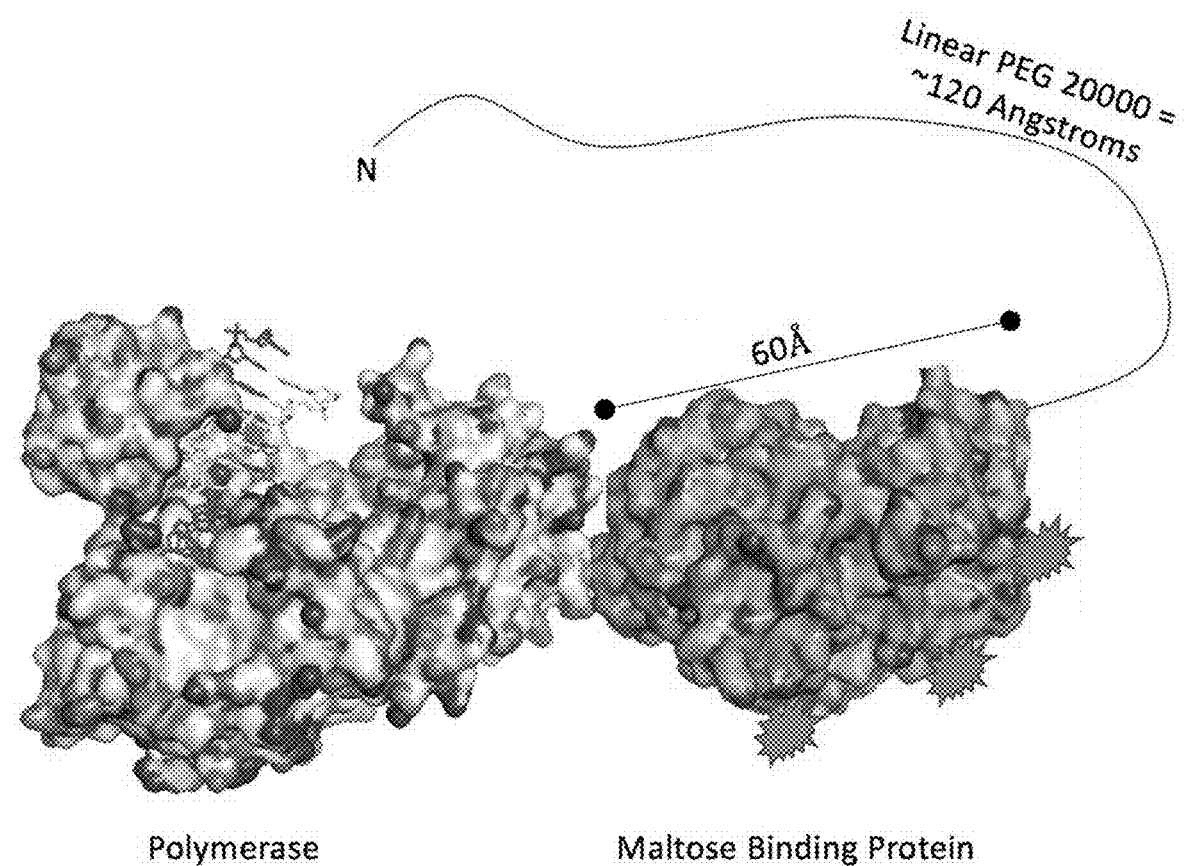
FIG. 5 provides a schematic illustration of the structure of a nucleotide-tethered polymerase-maltose binding protein fusion complex.

Alternatively, in some exemplary embodiments, the heterobifunctional linker may contain, e.g., a maltose group, a biotin group, an O2-benzylcytosine group or O2-benzylcytosine derivative, an O6-benzylguanine group, or an O6-benzylguanine derivative. The NHS group of a linker may then react with a primary amine on a nucleotide, thereby creating a covalent attachment without modifying or destroying the maltose group, biotin group, O2-benzylcytosine group or O2-benzylcytosine derivative, O6-benzylguanine group, or O6-benzylguanine derivative. Such a functionalized nucleotide may then be covalently or non-covalently attached to the enzyme by reaction of the maltose group, biotin group, O2-benzylcytosine group or O2-benzylcytosine derivative, O6-benzylguanine group, or O6-benzylguanine derivative with a suitable functional group or binding partner attached to the enzyme. For example, FIG. 5 illustrates the tethering of a nucleotide to a polymerase-maltose binding protein fusion complex using a linear PEG linker comprising a maltose group at one end.

Branched PEG molecules allow for simultaneous coupling of protein, dye(s), and nucleotide(s), such that multiple aspects of the compositions described herein may be present within a single reagent. Examples of suitable branched PEG molecules include, but are not limited to, PEG molecules comprising at least 4 branches, at least 8 branches, at least 16 branches, or at least 32 branches. Alternatively, it is contemplated that each individual element may be provided separately.

The length of the linker may vary depending on the type of nucleotide (or other base-pairing moiety) and the enzyme (or other nucleic acid binding moiety). In some instances, the enzyme linked nucleotide should have a length effective to allow the nucleotide or nucleotide analog to pair with a complementary nucleotide while precluding incorporation of the nucleotide or nucleotide analog into the 3' end of a polynucleotide. In some instances, the linker length in the enzyme linked nucleotide is different for each different nucleotide or nucleotide analog. In some instances, the length of the linker will be defined as its persistence length, corresponding to the root-mean-square (RMS) distance between the ends of the linker as characterized by dynamic simulations, 2-D trapping experiments, or ab initio calculations based on statistical distributions of polymers in compact, collapsed, or fluid states as required by the solution, suspension, or fluid conditions present. In some instances, a linker may have persistence length from 0.1 to 1,000 nm, from 0.6 to 500 nm, for from 0.6 to 400 nm. In some instances, a linker may have a persistence length of 0.6, 3.1, 12.7, 22.3, 31.8, 47.7, 95.5, 190.9, 381.8, 763.8 nm, or 989.5 nm or a range defined by or comprising any two or more of these values. In some instances, a linker may have a persistence length of at least 0.1, at least 0.2, at least 0.4, at least 1, at least 2, at least 4, at least 10, at least 20, at least 30, at least 40, at least 50, at least 60, at least 80, at least 90, at least 100, at least 200, at least 300, at least 400, at least 500, at least 700, or at least 1,000 nm, or a persistence length in a range defined by or comprising any two or more of these values. In some instances, linkers provided for one nucleotide may be longer or shorter than the linker provided for another nucleotide. For example, in some instances, dTTP may be linked to a nucleic acid binding moiety thought a longer linker than is used to tether dGTP, or vice versa.

In some instances, a linker for connecting T to the enzyme can have a persistence length of about 0.1-1,000 nm, 0.5-500 nm, 0.5-400 nm, 0.5-300 nm, 0.5-200 nm, 0.5-100 nm, 0.5-50 nm, 0.6-500 nm, 0.6-400 nm, 0.6-300 nm, 0.6-200 nm, 0.6-100 nm, 0.6-50 nm, 1-500 nm, 1-400 nm, 1-300 nm, 1-200 nm, 1-100 nm, 1.5-500 nm, 1.5-400 nm, 1.5-300 nm, 1.5-200 nm, 1.5-100 nm, 1.5-50 nm, 1-50 nm, 5-500 nm, 5-400 nm, 5-300 nm, 5-200 nm, 5-100 nm, or 5-50 nm. In some instances, a linker may have a persistence length of about 0.1, 0.5, 0.6, 1.0, 1.5, 1.8, 2.0, 2.5, 3.0, 3.1, 4.0, 5.0, 6.0, 7.0, 8.0, 9.0, 10.0, 12.7, 22.3, 31.8, 47.7, 95.5, 190.9, or 381.8 nm, or a persistence length in a range defined by or comprising any two or more of these values. In some instances, a linker may have a persistence length of greater than about 0.1, 0.5, 0.6, 1.0, 1.5, 1.8, 2.0, 2.5, 3.0, 3.1, 4.0, 5.0, 6.0, 7.0, 8.0, 9.0, 10.0, 12.7, 22.3, 31.8, 47.7, 95.5, 190.9, or 381.8 nm. In some instances, the linker may have a persistence length of shorter than about 5, 10, 20, 30, 40, 50, 60, 80, 100, 200, 300, 400, 500, 700, or 1,000 nm. In some instances, a linker may have a persistence length of 0.1, 0.2, 0.4, 1, 2, 4, 10, 20, 30, 40, 50, 60, 80, 100, 200, 300, 400, 500, 700, or 1,000 nm, or a persistence length in a range defined by or comprising any two or more of these values. In some instances, the linkers provided for T can be longer than for A, G, or C. In some instances, the linkers provided for T can be shorter than for A, G, or C. In some instances, the linkers provided for T can be the same length as those for A, G, or C.

In some instances, a linker for connecting A to the enzyme can have a persistence length of about 0.1-1,000 nm, 0.5-500 nm, 0.5-400 nm, 0.5-300 nm, 0.5-200 nm, 0.5-100 nm, 0.5-50 nm, 0.6-500 nm, 0.6-400 nm, 0.6-300 nm, 0.6-200 nm, 0.6-100 nm, 0.6-50 nm, 1-500 nm, 1-400 nm, 1-300 nm, 1-200 nm, 1-100 nm, 1.5-500 nm, 1.5-400 nm, 1.5-300 nm, 1.5-200 nm, 1.5-100 nm, 1.5-50 nm, 1-50 nm, 5-500 nm, 5-400 nm, 5-300 nm, 5-200 nm, 5-100 nm, or 5-50 nm. In some instances, a linker may have a persistence length of about 0.1, 0.5, 0.6, 1.0, 1.5, 1.8, 2.0, 2.5, 3.0, 3.1, 4.0, 5.0, 6.0, 7.0, 8.0, 9.0, 10.0, 12.7, 22.3, 31.8, 47.7, 95.5, 190.9, or 381.8 nm, or a persistence length in a range defined by or comprising any two or more of these values. In some instances, a linker may have a persistence length of greater than about 0.1, 0.5, 0.6, 1.0, 1.5, 1.8, 2.0, 2.5, 3.0, 3.1, 4.0, 5.0, 6.0, 7.0, 8.0, 9.0, 10.0, 12.7, 22.3, 31.8, 47.7, 95.5, 190.9, or 381.8 nm. In some instances, the linker may have a persistence length of shorter than about 5, 10, 20, 30, 40, 50, 60, 80, 100, 200, 300, 400, 500, 700, or 1,000 nm. In some instances, a linker may have a persistence length of 0.1, 0.2, 0.4, 1, 2, 4, 10, 20, 30, 40, 50, 60, 80, 100, 200, 300, 400, 500, 700, or 1,000 nm, or a persistence length in a range defined by or comprising any two or more of these values. In some instances, the linkers provided for A can be longer than for T, G, or C. In some instances, the linkers provided for A can be shorter than for T, G, or C. In some instances, the linkers provided for A can be the same length as those for T, G, or C.

In some instances, a linker for connecting C to the enzyme can have a persistence length about 0.1-1,000 nm, 0.5-500 nm, 0.5-400 nm, 0.5-300 nm, 0.5-200 nm, 0.5-100 nm, 0.5-50 nm, 0.6-500 nm, 0.6-400 nm, 0.6-300 nm, 0.6-200 nm, 0.6-100 nm, 0.6-50 nm, 1-500 nm, 1-400 nm, 1-300 nm, 1-200 nm, 1-100 nm, 1.5-500 nm, 1.5-400 nm, 1.5-300 nm, 1.5-200 nm, 1.5-100 nm, 1.5-50 nm, 1-50 nm, 5-500 nm, 5-400 nm, 5-300 nm, 5-200 nm, 5-100 nm, or 5-50 nm. In some instances, a linker may have a persistence length of about 0.1, 0.5, 0.6, 1.0, 1.5, 1.8, 2.0, 2.5, 3.0, 3.1, 4.0, 5.0, 6.0, 7.0, 8.0, 9.0, 10.0, 12.7, 22.3, 31.8, 47.7, 95.5, 190.9, or 381.8 nm, or a persistence length in a range defined by or comprising any two or more of these values. In some instances, a linker may have a persistence length of greater than about 0.1, 0.5, 0.6, 1.0, 1.5, 1.8, 2.0, 2.5, 3.0, 3.1, 4.0, 5.0, 6.0, 7.0, 8.0, 9.0, 10.0, 12.7, 22.3, 31.8, 47.7, 95.5, 190.9, or 381.8 nm. In some instances, the linker may have a persistence length of shorter than about 5, 10, 20, 30, 40, 50, 60, 80, 100, 200, 300, 400, 500, 700, or 1,000 nm. In some instances, a linker may have a persistence length of 0.1, 0.2, 0.4, 1, 2, 4, 10, 20, 30, 40, 50, 60, 80, 100, 200, 300, 400, 500, 700, or 1,000 nm, or a persistence length in range defined by or comprising any two or more of these values. In some instances, the linkers provided for C can be longer than for A, T, or G. In some instances, the linkers provided for C can be shorter than for A, T, or G. In some instances, the linkers provided for C can be the same length as those for A, T, or G.

In some instances, a linker for connecting G to the enzyme can have a persistence length about 0.1-1,000 nm, 0.5-500 nm, 0.5-400 nm, 0.5-300 nm, 0.5-200 nm, 0.5-100 nm, 0.5-50 nm, 0.6-500 nm, 0.6-400 nm, 0.6-300 nm, 0.6-200 nm, 0.6-100 nm, 0.6-50 nm, 1-500 nm, 1-400 nm, 1-300 nm, 1-200 nm, 1-100 nm, 1.5-500 nm, 1.5-400 nm, 1.5-300 nm, 1.5-200 nm, 1.5-100 nm, 1.5-50 nm, 1-50 nm, 5-500 nm, 5-400 nm, 5-300 nm, 5-200 nm, 5-100 nm, or 5-50 nm. In some instances, a linker may have a persistence length of about 0.1, 0.5, 0.6, 1.0, 1.5, 1.8, 2.0, 2.5, 3.0, 3.1, 4.0, 5.0, 6.0, 7.0, 8.0, 9.0, 10.0, 12.7, 22.3, 31.8, 47.7, 95.5, 190.9, or 381.8 nm, or a persistence length in a range defined by or comprising any two or more of these values. In some instances, a linker may have a persistence length of greater than about 0.1, 0.5, 0.6, 1.0, 1.5, 1.8, 2.0, 2.5, 3.0, 3.1, 4.0, 5.0, 6.0, 7.0, 8.0, 9.0, 10.0, 12.7, 22.3, 31.8, 47.7, 95.5, 190.9, or 381.8 nm. In some embodiments, the linker may have a persistence length of shorter than about 5, 10, 20, 30, 40, 50, 60, 80, 100, 200, 300, 400, 500, 700, or 1,000 nm. In some instances, a linker may have a persistence length of 0.1, 0.2, 0.4, 1, 2, 4, 10, 20, 30, 40, 50, 60, 80, 100, 200, 300, 400, 500, 700, or 1,000 nm, or a persistence length in a range defined by or comprising any two or more of these values. In some instances, the linkers provided for G can be longer than for A, T, or C. In some instances, the linkers provided for G can be shorter than for A, T, or C. In some instances, the linkers provided for G can be the same length as those for A, T, or C.

Suitable nucleic acid binding moieties: Suitable nucleic acid binding moieties according to the compositions and methods of the present disclosure comprise any nucleic acid binding moiety that is capable of binding to a nucleic acid, and in particular an elongating nucleic acid, such that the binding complex may incorporate one or more specifically base-paired nucleotides or nucleosides. For example, a suitable nucleic acid binding moiety may incorporate a moiety that binds to a nucleic acid at a site of elongation or replication, or at the site of a replication or elongation complex. Exemplary nucleic acid binding moieties may include, for example, a DNA polymerase or a catalytic domain or fragment thereof, an RNA polymerase or a catalytic domain or fragment thereof, a reverse transcriptase or a catalytic domain or fragment thereof, a helicase or a catalytic domain or fragment thereof, an endonuclease or a catalytic domain or fragment thereof (including a CRISPR-associated endonuclease, for example CAS-6 or CAS-9), an exonuclease or fragment thereof, a nucleotidyl-transferase or a catalytic domain or fragment thereof, a telomerase or a catalytic domain or fragment thereof, or any other enzyme, protein or nucleic acid domain, or moiety as is or may be known in the art to be capable of binding to or recognizing nucleic acid molecules, and especially wherein such recognition includes the binding and/or stabilization of a complex comprising at least one nucleotide or nucleoside that is not incorporated into a nucleic acid chain. Exemplary polymerases may include, but are not limited to, E. coli Pol I, Klenow fragment, 9° N polymerase, Therminator® polymerase Taq polymerase, Pfu polymerase, Bsu polymerase, Bst polymerase, Klentaq® polymerase, and any combination or variant thereof, or any other bacterial, viral, eukaryotic, or other polymerase known in the art to be capable of forming a complex incorporating a nucleic acid and at least one specifically base paired nucleotide or nucleoside. Exemplary reverse transcriptases may include, but are not limited to, Moloney Murine Leukemia Virus (MMLV) reverse transcriptase, HIV group O reverse transcriptase, HIV group M reverse transcriptase, Hepatitis B virus (HBV) reverse transcriptase, Hepatitis C virus (HCV) reverse transcriptase, avian myeloblastosis virus (AMV) reverse transcriptase, or other viral, bacterial, or eukaryotic reverse transcriptase known in the art to be capable of forming a complex incorporating a nucleic acid and at least one specifically base paired nucleotide or nucleoside.

Nucleic acid binding moiety (e.g., enzyme) linker conjugation: Conjugation of the linker to the enzyme, protein, or nucleic acid binding moiety may be accomplished using any of a variety of methods known in the art. See, for example, Lundblad, R., Chemical Reagents for Protein Modification, 4th Edition, CRC press, 2014, the contents of which are hereby incorporated by reference in their entirety and especially with regard to their disclosure of reagents and methods for the modification of protein surfaces. For example, linkage of a PEG functionalized nucleotide to an enzyme may be accomplished using standard maleimide-cysteine conjugation chemistry. According to this method, one or more cysteine residues are introduced into the enzyme of interest using site-directed mutagenesis or other methods. Under mild basic conditions, the maleimide will react with the free thiol group of the cysteine, thereby forming a covalent linkage that is highly specific. In some embodiments, placement of the cysteine in the enzyme's amino acid sequence can be optimized to allow the tethered nucleotide to reach the active site without perturbing enzyme structure or function.

Alternatively, branched PEG molecules containing only terminal NHS groups can simultaneously be reacted with either native or engineered lysine residues on the surface of the enzyme or protein, with $NH_2$ labeled nucleotides (as described above), and with $NH_2$ labeled dye molecules. The result is a single pot reaction where conditions can be optimized to coordinate the formation of the complete complex.

Labeling the nucleic acid binding moiety (e.g., enzyme) with a fluorescent reporter: A variety of fluorophores with visible light emission spectra are available to act as reporters for detection of template-bound enzyme-nucleotide conjugates. These fluorescent dyes include, but are not limited to, cyanine dye 3 (Cy3), cyanine dye 3.5 (Cy3.5), cyanine dye 5 (Cy5), cyanine dye 5.5. (Cy5.5), Alexa Fluor 532, Alexa Fluor 594, Alexa Fluor 647, and Alexa Fluor 660. In some embodiments, the dye molecules also contain an appropriate reactive group to allow conjugation to the enzyme, in some cases using a reaction mechanism that is orthogonal to cysteine-maleimide conjugation chemistry. Examples of these chemistries include: amine-, aldehyde-, or carboxylic acid-reactive conjugation chemistries. The target enzyme (or other nucleic acid binding moiety) can be reacted with these dyes to produce a dye-labeled enzyme or enzyme conjugate containing from 1 to about 100, or more than 100 attached dye molecules. In other embodiments, the enzyme may be fused to a secondary protein that provides labeling sites for attachment of fluorescent dyes. Dyes may also be non-covalently associated with the target enzyme or DNA binding moiety. In some instances, one or more streptavidin-enzyme conjugates, for example, may be used with biotinylated dyes to make protein conjugates with the appropriate fluorescence.

In some instances, each type of nucleotide linked enzyme can be labeled with a unique dye such that binding of the correct nucleotide to the template DNA produces a fluorescence signal of a unique wavelength and intensity relative to the other 3 nucleotide-protein-dye complexes.

In some instances, each nucleic acid binding composition that comprises a unique base-pairing moiety may comprise a unique detectable tag. Examples of suitable tags include, but are not limited to, fluorophores, quantum dots, Raman tags, up-converting phosphors, chemiluminescent tags, and the like.

Other conjugate components: In addition to the nucleotides and other exemplary base-pairing moieties discussed above, additional elements which may be assembled into the compositions and reagents disclosed herein, for use according to the methods disclosed herein, may comprise one or more of the following:

PEG and other polymer linkers: As noted above, the present disclosure contemplates the use of PEG based linkers or other linkers of various lengths to create nucleic acid binding moiety—base-pairing moiety conjugates. In some instances, linkers may comprise linear PEGs (e.g., linear PEGs of about 300 Da, 400 Da, 600 Da, 800 Da, 1000 Da, 2000 Da, 3000 Da, 4000 Da, 5000 Da, 10000 Da, 20000 Da, 40000 Da, 80000 Da, or 120000 Da molecular weight (MW), or of any molecular weight within this range). In some instances, a linker may comprise polyethylene glycol having sizes of PEG-88 Da, PEG-484 Da, PEG-2K Da, PEG-3.5K Da, PEG-5K Da, PEG-7.5K Da, PEG-10K Da, PEG-15K Da, PEG-30K Da, PEG-60K Da, PEG-100K Da, PEG-150K Da, or PEG-200K Da, or larger. In some instances, PEG linkers may also be branched, containing, e.g., 3, 4, 6, 8, 12, or more arms, and may have molecular weights in the same size ranges as described above. Branched PEG linkers provide the added benefit of conjugating the enzyme, dye molecules, and nucleotides in a single pot reaction using the same amine-reactive NHS chemistry at all sites. Similar linkers may be constructed comprising other polymers, such as polyethylene glycol (PEG), polypropylene glycol (PPG), polyethylene (PE), polypropylene (PP), polyamides, polyesters, polylactic acid, polyglycolic acid, polylactic/glycolic acid, polypropylene glycol (PPG), polyvinyl acetate (PVA), as well as other linear and branched polymers as are known in the art. The present disclosure also contemplates the use of block copolymers, such as polyethylene/polypropylene/polyethylene glycol and PPG/PEG/PPG copolymers, for example, the Pluronic® series of block copolymers.

Peptide linkers: The present disclosure contemplates peptide linkers of various length and composition. Peptide linkers may be attached via protein surface residues as described elsewhere herein, or may be attached at the N- or C-terminus of the expressed polymerase, enzyme, or nucleic acid binding moiety.

As in the case of other linkers, peptide linkers can be of varying length to control relative nucleotide concentrations and/or the accessibility of bound nucleotide or nucleotide analogs for complex formation. In some instances, the peptide linker may comprise from about 10 to about 1000 amino acid residues. In some instances, the peptide linker may comprise at least 10, at least 20, at least 30, at least 40, at least 50, at least 60, at least 70, at least 80, at least 90, at least 100, at least 200, at least 300, at least 400, at least 500, at least 600. at least 700, at least 800, at least 900, or at least 1000 amino acid residues. In some instances, the peptide linker may comprise at most 1000, at most 900, at most 800, at most 700, at most 600, at most 500, at most 400, at most 300, at most 200, at most 100, at most 90, at most 80, at most 70, at most 60, at most 50, at most 40, at most 30, at most 20, or at most 10 amino acid residues. Any of the lower and upper values described in this paragraph may be combined to form a range included within the present disclosure, for example, in some instances the peptide linker may comprise from about 30 amino acid residues to about 200 amino acid residues. Those of skill in the art will recognize that length of the peptide linker may have any value within this range, e.g., about 126 amino acid residues.

In some instance, the peptide linker may comprise a series of amino acid residues selected from any group of amino acids including, but not limited to, L-amino acids, D-amino acids, non-natural amino acids, amino acid analogs, and the like. In some instances, the peptide linker may comprise a single type of amino acid, e.g., poly-L-glycine or poly-L alanine. In some instances, the peptide linker may comprise any combination of or any sequence of L-amino acids, D-amino acids, non-natural amino acids, amino acid analogs, and the like.

In some instances, peptide linkers may be attached to a polymerase or nucleic acid binding moiety via a single (or multiple) amino acid residues suitable for conjugation (commonly a lysine or cysteine residue). Alternatively, a peptide or polypeptide linker may be genetically fused to a polymerase or nucleic acid binding moiety. A linker may comprise or may further comprise a fusion of an enzyme, a polymerase, or a nucleic acid binding moiety with a another protein or protein domain, such as a maltose binding protein (MBP), an O-6-methylguanine-DNA methyltransferase, or a variant thereof such as a SNAP-tag or CLIP-tag molecule, an avidin or a streptavidin molecule, or any such protein, protein domain, or polypeptide as may provide a site for attachment of a linker. The polypeptide fusion or Pol fusion protein can then be site-specifically labeled with the nucleotide or other base-pairing moiety, providing a spacer which increases the effective distance between the nucleotide and the nucleic acid binding moiety. Preferably, such a polypeptide fusion protein will incorporate a site or means for attachment of a polymer linker to which a nucleotide, fluorescent label, blocked nucleotide, labeled nucleotide, or the like, can be attached. For example, MBP-Pol can be expressed with a single cysteine on the surface of MBP at positions 29 or 137, or 322. The cysteine residue can then be labeled with a PEG-Nucleotide using sulfhydryl-reactive maleimide conjugation chemistry to effectively produce a MBP-PEG linker. In another example, SNAP-Pol can be expressed, and a linker comprising a PEG or other linker, conjugated to a nucleotide, labeled nucleotide, or blocked nucleotide, and further conjugated to a methylguanine residue, allowing attachment of the linker via the methylguanine moiety to the SNAP domain of the Pol fusion. Similarly, in another example, streptavidin-Pol may be produced, allowing the attachment of biotinylated linkers to the streptavidin-Pol fusion. Other binding domains may be used in a similar manner to provide linkages to activated linker constructs, including such interacting moieties as antibodies and affinity tags, His tags (e.g., His 6×, His 8×, His 10×, or His 12×), etc.

Nucleic acid linkers: Nucleic acid or polynucleotide linkers also can be used, comprising single-stranded DNA (ssDNA), single-stranded RNA (ssRNA), double-stranded DNA (dsDNA), ssDNA/ssRNA hybrids, peptide nucleic acids (PNA), or combinations or variants thereof, which can further comprise repeats of a single nucleotide (such as polyT, polyC, polyA, polyG, or polyU) or sequences selected or designed to provide attachment sites for accessory proteins, tags, or cognate nucleic acid molecules and/or any moieties attached thereto. For example, a fluorescent tag, epitope tag, radio-label, or spin label may be attached to a single stranded nucleic acid sequence whose complementary sequence is within the sequence of the linker molecule. In another example, CAS-9, CAS-6, or other DNA-targeting molecules may be targeted using known methods to sequences within the sequence of the linker molecule. In some instances, the use of non-natural nucleotides is contemplated.

Other linkers: Linkers can be comprised of any molecule that provides sufficient length or intramolecular spacing to provide the nucleotide with enough volume to explore the space surrounding the polymerase active site that the effective local concentration of nucleotide and resulting shift in binding equilibria for enzyme-nucleotide conjugates comprising the correct nucleotide provides sequence discrimination between the four bases. Polymers, peptides, nucleic acids, and polysaccharides are examples of such linkers, but other linear or short-branched polymers as are known in the art will also provide an equivalent function and are expressly contemplated herein. For example, polymers of ribose, deoxyribose, fructose, glucose, lactose, or the like, or derivatives thereof, such as cellulose, cellulose acetate, or the like, may comprise suitable linkers within the compositions and methods as disclosed herein.

Proteins: Polymerases or other nucleic acid binding proteins can be labeled with PEG-nucleotides on surface lysine residues using NHS chemistry. Alternatively or additionally, a cysteine mutation can be introduced to the polymerase and maleimide chemistry can be used to provide labeling specificity. Other linkages, such as linkages to serine, threonine, tyrosine, histidine or arginine residues, or to phosphorylated variants thereof, are known in the art and are contemplated within the compositions and methods of the present disclosure.

The compositions and methods disclosed herein, in some embodiments, may make use of high polymerase-DNA binding, enzyme-DNA binding, or DNA binding to a DNA-binding moiety in the presence of the correct nucleotide at the N+1 position or the position to be measured. The compositions and methods disclosed herein, in some embodiments, may also make use of low polymerase-DNA binding, enzyme-DNA binding, or DNA binding to a DNA-binding moiety in the absence of the correct nucleotide. This can be achieved, for example, by increasing the ionic strength of the buffer to promote dissociation, or by mutation to the polymerase thus reducing the natural polymerase-DNA affinity.

Tuning binding to provide nucleotide discrimination for the templating base: Any of the methods disclosed herein can be used to tune the system such that the Pol-Linker-Nucleotide complex (i.e., a nucleic acid binding composition or conjugate) containing the correct base will preferentially bind to the target DNA with high discrimination for only the correct base. This tuning can be accomplished, for example, by lengthening or shortening the linker between the nucleotide and the protein to effectively reduce the nucleotide concentration around the protein active site.

Figure 6:
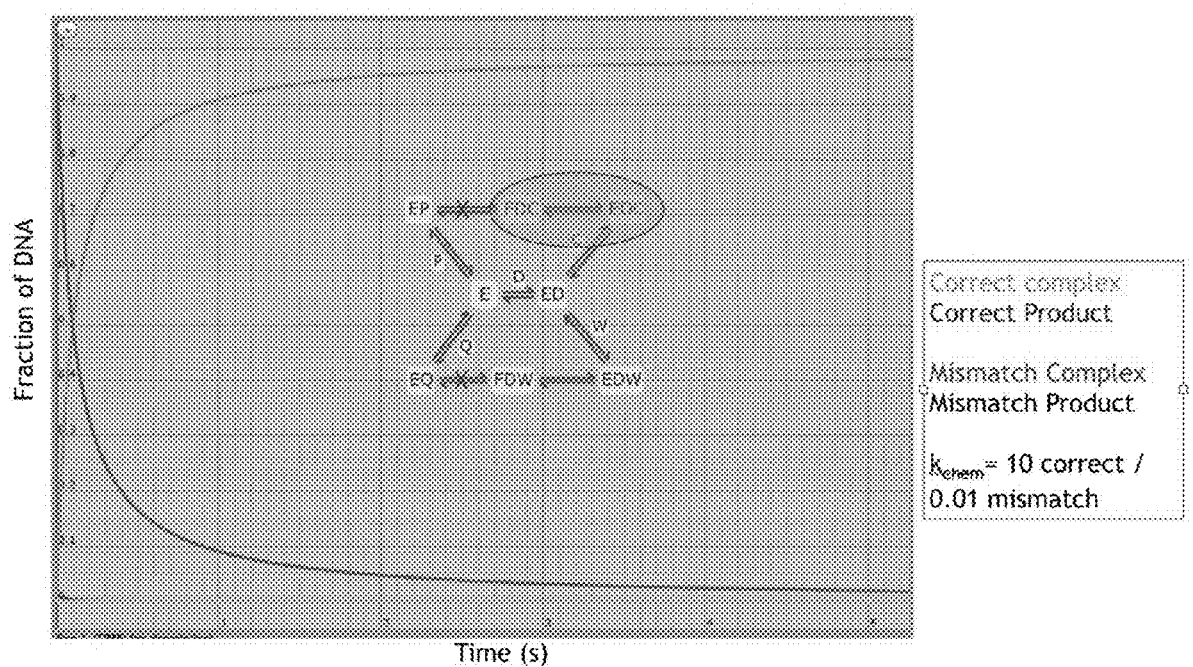
FIG. 6 provides an illustration of the fraction of template DNA molecules with bound enzyme-PEG-nucleotide conjugate when the nucleotide is the correct N+1 nucleotide (green trace, "C" in the pathway) vs. the incorrect N+1 nucleotide (red trace, "W" in the pathway) when $k_{chem}$=1,000 (e.g., 10 correct base-pairing events for every 0.01 mismatched base-pairing events).

Alternatively, in some instances, it may be preferred to pair mutations at the active site with natural or modified nucleotides such that 4 base discrimination is achieved. For example, FIG. 6 provides a plot of the fraction of template DNA molecules with bound enzyme-PEG-nucleotide conjugate when the N+1 nucleotide is the correct nucleotide (green trace, "C" in the pathway) vs. the incorrect N+1 nucleotide (red trace, "W" in the pathway) when $k_{chem}=0$. Binding of the correct nucleotide complex is kinetically favored and rapidly (~1s) becomes the dominant population that can be imaged for base calling.

In some instances, discrimination for the templating base is achieved through a combination of tuning of linker length, mutational tuning of active site binding affinity, and/or the use of modified nucleotides. It is a surprising finding of the present disclosure, for example, that greater discrimination for the probing base is obtained through the use of ribonucleotides rather than deoxyribonucleotides, despite the reduced affinity ribonucleotides show for DNA-Pol complexes. It is a further surprising finding of the present disclosure that each ribonucleotide, deoxyribonucleotide, or nucleoside has a different optimal linker length for base discrimination; i.e., each linker for each nucleotide must be separately optimized to provide the ideal discrimination power for each application, such as DNA sequencing.

Using nucleotide-linked enzymes for sequencing: In some exemplary embodiments, a method of utilizing nucleotide-linked enzymes for DNA sequencing may proceed through one or more steps as follows. After exposing the template DNA in question to these complexes, in some instances, DNA may be bound predominantly with enzyme-linked nucleotide conjugates that contain the correct cognate base. DNA, which may be present in a tethered form or in clonally-amplified clusters tethered to a surface, may then be imaged to determine which base is present at the N+1 position. After detection, buffer conditions that promote enzyme dissociation (EDTA, high salt, etc.) may be applied to remove the bound enzyme-conjugated nucleotides (and associated fluorescent signal). The N+1 base position may then be used to incorporate a 3' blocked reversible terminator. In some embodiments, the 3' blocking group may then be reacted to form a 3' hydroxyl, and in some further embodiments, the next base may then be detected in cyclic fashion.

In some instances, a polymerase used as the nucleic acid binding moiety may be blocked from extending the primer chain by a temporary block, such as the use of a catalytically inactive nucleotide. In some instances, a polymerase may be prevented from extending the primer chain by the use of a blocked nucleotide. In some instances, a polymerase may be prevented from extending the primer chain by the use of a nucleotide with a blocking moiety at the 5' position of the sugar group of the nucleotide. In some instances, a polymerase may be prevented from extending the primer chain by the use of a nucleotide with a blocking moiety at the 3' position of the sugar group of the nucleotide, such as, for example, attached to the 3' carbon or the 3' oxygen of the ribose, deoxyribose, or equivalent sugar group of a nucleotide. In some instances, a polymerase may be prevented from extending the primer chain by the use of a nucleotide with a blocking moiety at a position other than the 3' or 5' position of the sugar group of the nucleotide. In some instances, the blocking group may comprise an azido group, an azidomethyl group, an aminoallyl group, an aminoalkyl, a benzyl group, a malonyl group, a maleimidyl group, an amino group, a secondary amine, a tertiary amine, a quaternary amine, a disulfide ethyl, a disulfide t-butyl, any disulfide linked group, 3'-O-azido, a 3'-O-methyl-azido, 3'-O-amino, 3'-O-aminoallyl, phosphorothioate, or any other blocking group known in the art of nucleotide chemistry for the reversible blocking of reactivity at the 3' carbon of a ribonucleotide or deoxyribonucleotide moiety, wherein removal of the blocking group results in the presence of a hydroxyl at the 3' position. In some instances, the blocking group may be one that is removable by acid cleavage, by base cleavage, by metal catalyzed (e.g., palladium) cleavage, by enzymatic cleavage, or by other methods as are known in the art for the removal of blocking groups from nucleic acids.

In some instances, a blocking group may comprise, include, or incorporate the linker to the polymerase. In some instances, nucleotides may be linked to a polymerase using a cleavable linker. In some instances, a polymerase may be blocked from extending the primer chain by maintaining buffer conditions lacking cofactors or salts required for polymerase activity, or by substituting a non-catalytic salt or a salt that inhibits catalysis, such as calcium, or strontium.

In some instances, extension of the primer chain by one residue may be achieved by alleviating the temporary block on chain extension, such as, for example, by altering buffer conditions to include magnesium or manganese and/or by cleaving a blocking group from the bound nucleotide. In some instances, the linker may be cleaved in such a manner as to render the bound nucleotide competent for primer extension. In some further instances, the polymerase may be, or may be rendered (such as by a change in buffer conditions) competent to catalyze chain extension.

In some instances, unbound polymerase may be washed away in between any step, thus reducing, eliminating, or substantially eliminating nonspecific binding, spurious detection events, or uncontrolled primer extension. In some instances, labels or detectable moieties may be attached through a labile bond or cleavable linker, wherein said labile bond or cleavable linker may be cleaved to allow release of the label or detectable moiety, thereby reducing spurious detection events or background signal, such as background fluorescence, in any given sequencing cycle. In some instances, a cleavable linker may be acid labile, base labile, or subject to enzymatic cleavage or to release of a noncovalent linkage. In some instances, a linker may be attached via a disulfide, amino, thioester, ester, or amide linkage. In some instances, blocking of the extending chain may be achieved by the incorporation of a blocked nucleotide as disclosed herein prior to the addition of a catalytically incompetent or catalytically blocked polymerase, enzyme, or nucleic acid binding moiety. In some instances, blocking of the extending chain may be achieved by the incorporation of a blocked nucleotide as disclosed herein concurrently with the addition of a catalytically incompetent or catalytically blocked polymerase, enzyme, or nucleic acid binding moiety. In some instances, blocking of the extending chain may be achieved by the incorporation of a blocked nucleotide as disclosed herein following the addition of a catalytically incompetent or catalytically blocked polymerase, enzyme, or nucleic acid binding moiety. In some instances, blocking of the extending chain may be achieved by the incorporation of a blocked nucleotide as disclosed herein independent of or without the addition of a catalytically incompetent or catalytically blocked polymerase, enzyme, or nucleic acid binding moiety. Addition and/or incorporation of blocked nucleotides may provide the benefit of ensuring that elongation of most, all, or substantially all elongating nucleic acid chains within a sample occurs in the same register, i.e., that each elongating chain maintains the same length as every other at each iteration of the elongation and/or sequencing cycle.

Multipart reagents having increased avidity for polymerase binding: In some instances, a base-pairing moiety (such as a nucleotide or nucleotide analog) may be provided separately from a nucleic acid binding moiety (such as a polymerase). Briefly, and without intending to be bound by any particular theory, an increase in binding of a substrate to an enzyme or an enzyme complex can be affected by increasing the effective concentration of substrate as described elsewhere herein. Such an increase may be caused by increasing the concentration of substrate in free solution, or by increasing the amount of substrate in proximity to the relevant binding site. Such an increase may result from tethering a substrate or ligand (e.g., a nucleotide or nucleotide analog) to an active site or binding site of a nucleic acid binding moiety as described elsewhere herein, or by providing a composition which creates a local increase in substrate or ligand concentration by physically restricting a number of possible substrates or ligands into a limited volume. Such a construct or composition may thus bind to the binding site or active complex with a higher apparent avidity than would be observed with unlinked, untethered, or otherwise unrestricted individual substrates. One exemplary means of effecting such restriction is by providing a composition in which one or more substrates, and preferably multiple substrates, is bound to a particle such as a polymer, a branched polymer, a dendrimer, or a particle. The present disclosure therefore contemplates compositions comprising one or more nucleotides or nucleotide analogs bound in proximity by attachment to a polymer, branched polymer, dendrimer, particle, or equivalent structure. In some embodiments according to the methods and compositions of the present disclosure, contacting said composition or compositions with a nucleotide binding moiety such as a polymerase bound to a primed nucleic acid as described elsewhere herein, may result in the formation of a ternary complex which may be detected by fluorescence, for example, or by other means, in such a manner as to all the identity of one or more bases of said nucleic acid to be determined.

In some embodiments, a nucleotide or nucleotide analog may be linked such as through a tether to one or more additional nucleotides or nucleotide analogs. In some embodiments, a composition is provided which comprises one or more nucleotides or nucleotide analogs attached to one end or location of a polymer. In some embodiments, such polymers may include one or more of a PEG, a polypropylene, a polylactic acid, a polyglycolic acid, a polylactic/glycolic acid, a polyethylene/polypropylene copolymer, a block copolymer, a polypeptide, a polynucleotide, a polysaccharide, or any other polymer as is or may be known in the art or any combination thereof. In some embodiments, said polymer may comprise a linear polymer. In some embodiments, said polymer may comprise a branched polymer. In some embodiments, said polymer amy comprise a dendrimer. In some embodiments, said polymer may be oriented or composed such that the ends are not equivalent, i.e., such that the polymer has a recognizable polarity. In some embodiments, said polymer may be oriented or composed such that the ends are equivalent, i.e., such that the polymer does not recognizable polarity. In some embodiments, multiple polymer moieties may be attached to a central moiety or site such that the ends radiating therefrom are equivalent. In some embodiments, multiple polymer moieties may be attached to a central moiety or site such that the ends radiating therefrom are not equivalent. In some embodiments, multiple polymer moieties may be attached to a central moiety or site such that the polymer moieties radiating therefrom are of equivalent length and/or composition. In some embodiments, multiple polymer moieties may be attached to a central moiety or site such that the polymer moieties radiating therefrom differ in length and/or composition. In some embodiments, a composition is provided which further comprises one or more nucleotides or nucleotide analogs attached to an additional end or location of a polymer. In some embodiments, a composition is provided which further comprises one or more nucleotides or nucleotide analogs attached to multiple ends or locations of a polymer. In some embodiments, each nucleotide or nucleotide analog attached to an individual polymer, branched polymer, dendrimer, particle, or the like is the same nucleotide or nucleotide analog. In some embodiments, each nucleotide or nucleotide analog attached to an individual polymer, branched polymer, dendrimer, particle, or the like is not the same nucleotide or nucleotide analog. In one non-limiting example, a composition is provided comprising a branched polymer of 4, 8, 16, 32, or 64 PEG arms having attached to the ends thereof one or more nucleotides or nucleotide analogs, such that each end has attached thereto 0, 1, 2, 3, 4, 5, 6 or more nucleotides or nucleotide analogs. In one non-limiting example, a composition is provided comprising a branched polymer of between 3 and 128 PEG arms having attached to the ends thereof one or more nucleotides or nucleotide analogs, such that each end has attached thereto 0, 1, 2, 3, 4, 5, 6 or more nucleotides or nucleotide analogs. In some embodiments, a branched polymer or dendrimer has an even number of arms. In some embodiments, a branched polymer or dendrimer has an odd number of arms. In some embodiments, a composition is provided having attached thereto one or more fluorophores, spin labels, metals or metal ions, colorimetric labels, nanoparticles, PET labels, radioactive labels, or other such label as may render said composition detectable by such methods as are known in the art of the detection of macromolecules or molecular interactions. In some embodiments, said label may be attached to the nucleotide or nucleotide analog (e.g. by attachment to the 5' phosphate moiety of a nucleotide), to the polymer itself (e.g., to the PEG subunits), to an end of the polymer, to a central moiety, or to any other location within said polymer-nucleotide composition which would be recognized by one of skill in the art to be sufficient to render said composition, such as a particle, detectable by such methods as are known in the art or described elsewhere herein.

In some embodiments, the present disclosure contemplates contacting a composition comprising one or more nucleotides or nucleotide analogs as described elsewhere herein with one or more polymerases, catalytically inactive polymerases, catalytically active polymerases, reverse transcriptases, and/or other nucleotide binding moieties. In some embodiments, said contacting is optionally done in the presence of one or more nucleic acids. In some embodiments, said nucleic acids are single stranded nucleic acids. In some embodiments, said nucleic acids are primed single stranded nucleic acids. In some embodiments, said nucleic acids are double stranded nucleic acids. In some embodiments, said contacting comprises the contacting of said composition comprising one or more nucleotides or nucleotide analogs with one polymerase, catalytically inactive polymerase, catalytically active polymerase, reverse transcriptase, and/or other nucleotide binding moiety. In some embodiments, said contacting comprises the contacting of said composition comprising one or more nucleotides or nucleotide analogs with more than one polymerase, catalytically inactive polymerase, catalytically active polymerase, reverse transcriptase, and/or other nucleotide binding moiety. In some embodiments, said contacting comprises the contacting of said composition comprising one or more nucleotides or nucleotide analogs with multiple polymerases, catalytically inactive polymerases, catalytically active polymerases, reverse transcriptases, and/or other nucleotide binding moieties wherein said polymerases, catalytically inactive polymerases, catalytically active polymerases, reverse transcriptases, and/or other nucleotide binding moieties are bound to a single nucleic acid molecule. In some embodiments, said nucleic acid molecule may be in free solution, in suspension, in a viscous matrix such as, for example, an emulsion, a gel or a hydrogel, or attached to a surface. in some embodiments, said surface may be a treated or derivatized surface. In some embodiments, said surface may be optimized to provide low background binding or a high contrast to noise ratio (CNR) such as those surfaces described in described in co-pending U.S. patent application Ser. No. 16/363,842, incorporated by reference herein, and/or as described elsewhere herein.

In some embodiments, the present disclosure contemplates a method of identifying one or more nucleotides in a nucleic acid or an elongating nucleic acid chain by contacting a composition comprising one or more nucleotides or nucleotide analogs as described elsewhere herein with one or more polymerases, catalytically inactive polymerases, catalytically active polymerases, reverse transcriptases, and/or other nucleotide binding moieties. In one exemplary embodiment, one or more catalytically inactive polymerases may be bound to a nucleic acid in the presence of a composition comprising one or more nucleotides or nucleotide analogs as described elsewhere herein, wherein interaction between said composition and said polymerase, catalytically inactive polymerase, catalytically active polymerase, reverse transcriptase, and/or other nucleotide binding moiety stabilizes a ternary complex so as to render the complex detectable by fluorescence or by other methods as disclosed herein or otherwise known in the art. In a further embodiment, unbound nucleotide bearing polymer, etc. may optionally be washed away prior to detection of the labeled complex. In another embodiment, incorporation of a nucleotide or nucleotide analog may be achieved either by the removal of a blocking group from said nucleotide or nucleotide analog (such as by detachment of said nucleotide or nucleotide analog from its polymer, branched polymer, dendrimer, particle, or the like), or by the provision of a cofactor or activator such as a metal ion. In some embodiments, detection of the ternary complex is achieved prior to, concurrently with, or following the incorporation of the nucleotide residue. In some embodiments, a nucleic acid may comprise a nucleic acid with multiple primed locations for the attachment of polymerases and/or nucleic acid binding moieties. In some embodiments, multiple polymerases may be attached to a single nucleic acid molecule. In some embodiments, multiple polymerases may be bound to a composition as disclosed herein comprising multiple nucleotides or nucleotide analogs.

Fluorescence imaging for four base discrimination: Correctly identifying the next templating base can be achieved in a number of different modes. For example, any optical detection scheme and labeling configuration that allows discrimination between the 4 nucleotide species in a single imaging pass is ideal for this application. Several non-limiting examples are discussed below.

Two color excitation/four color emission: Enzyme-nucleotide conjugates can be configured so that each base is reported by a unique fluorescence signal. This may be achieved, for example, by using a set of fluorophores such that two of the conjugates are excited using a first excitation wavelength of light, and the other two conjugates are excited using a second excitation wavelength of light. Fluorescence can then be detected in four separate channels with filtering dependent on the emission wavelengths of the individual dyes. Examples of suitable excitation light sources and wavelengths, and fluorophore excitation and emission maxima, are illustrated in Table 1.

TABLE 1

Examples of excitation light sources/wavelengths and fluorophore excitation/emission maxima

| Excitation Source | Excitation Peak (Dye) | Emission Peak | Emission Peak Filter (Camera #) |
|---|---|---|---|
| 532 nm laser | 555 nm (Cy3) | 570 nm | 570 ± 10 nm (Camera 1) |
| 532 nm laser | 580 nm (Cy3.5) | 592 nm | 592 ± 10 nm (Camera 2) |
| 633 nm laser | 650 nm (Cy5) | 670 nm | 670 ± 10 nm (Camera 3) |
| 633 nm laser | 682 nm (Cy5.5) | 702 nm | 702 ± 10 nm (Camera 4) |

Two color excitation/two color emission: Alternatively, it is possible to detect binding of the enzyme-nucleotide conjugates described herein using two separate fluorophores excited by two different light sources. According to this scheme, in some instances, one of the conjugates can be labeled with both of the fluorophores creating an "on" state in both channels of detection, one of the conjugates can be labeled with one of the fluorophores thereby creating an "on" state in one detection channel, one of the conojugates can be labeled with the other fluorophore thereby creating an "on" state in the other detection channel, and one of the conjugates is not labeled thereby creating only "off" states in both detection channels. Alternatively, the conjugate labeled with two types of fluorophores can utilize FRET such that excitation of fluorophore with a shorter wavelength of light produces emission of the second fluorophore.

Additional modes of detection: In some instances, one of the conjugates may be in a dark state such that 3 unique detectable complexes are observed and the 4th signal is comprised of the absence of signal.

Reagents and kits: In some instances, the nucleic acid binding moiety—linker—base-pairing moiety compositions (i.e., nucleic acid binding conjugates or nucleic acid binding compositions) disclosed herein may constitute components of reagents or kits for performing nucleic acid sequencing or other nucleic acid detection and analysis applications.

In some instances, for example, a reagent of the present disclosure may comprise any of the nucleic acid binding compositions disclosed herein dissolved in a suitable buffer. In some instances, a reagent of the present disclosure may comprise any of the nucleic acid binding compositions disclosed herein dissolved in a suitable buffer at a specified concentration. Examples of suitable buffers include, but are not limited to, phosphate buffered saline, phosphate buffer, TAPS, MES, MOPS, or any combination of these. In some instances, the pH of the resulting solution may be buffered to any value within the range of about pH 5.0 to about pH 10.

In some instances, the reagent may comprise 1, 2, 3, 4, or more than 4 nucleic acid binding compositions, wherein each nucleic acid binding composition comprises a single type of base-pairing moiety, and wherein said base-pairing moiety comprises a nucleotide, nucleotide analog, nucleoside, or nucleoside analog. In some instances, the reagent may comprise 1, 2, 3, 4, or more than 4 nucleic acid binding compositions, wherein each nucleic acid binding composition comprises a single type of base-pairing moiety, and wherein said base-pairing moiety may respectively correspond to one or more from the group consisting of ATP, ADP, AMP, dATP, dADP, and dAMP; one or more from the group consisting of TTP, TDP, TMP, dTTP, dTDP, dTMP, UTP, UDP, UMP, dUTP, dUDP, and dUMP; one or more from the group consisting of CTP, CDP, CMP, dCTP, dCDP, and dCMP; and one or more from the group consisting of GTP, GDP, GMP, dGTP, dGDP, and dGMP. In some instances, the reagent may comprise 1, 2, 3, 4, or more than 4 nucleic acid binding compositions, wherein each nucleic acid binding composition comprises a single type of base-pairing moiety, and wherein said base-pairing moiety may respectively correspond to one or more from the group consisting of ATP, ADP, AMP, dATP, dADP, dAMP TTP, TDP, TMP, dTTP, dTDP, dTMP, UTP, UDP, UMP, dUTP, dUDP, dUMP, CTP, CDP, CMP, dCTP, dCDP, dCMP, GTP, GDP, GMP, dGTP, dGDP, and dGMP.

In some instances, a kit of the present disclosure may comprise any of the nucleic acid binding compositions and/or any of the reagents disclosed herein; one or more buffers; and instructions for the use thereof.

Systems: Also disclosed herein are systems configured for performing any of the disclosed nucleic acid sequencing or nucleic acid detection and analysis methods. In some instances, the disclosed systems may comprise one or more of the nucleic acid binding compositions and/or reagents described herein, one or more buffers, and/or one or more nucleic acid molecules tethered to a solid support.

In some instances, the system may further comprise a fluid flow controller and/or fluid dispensing system configured to sequentially and iteratively contact template nucleic acid molecules hybridized to nucleic acid molecules (e.g., adapters or primers) tethered to a solid support with the disclosed nucleic acid binding compositions and/or reagents. In some instances, said contacting may be performed within one or more flow cells. In some instances, said flow cells may be fixed components of the system. In some instances, said flow cells may be removable and/or disposable components of the system.

In some instances, the system may further comprise an imaging module, where the imaging module comprises, e.g., one or more light sources, one or more optical components (e.g., lenses, mirrors, prisms, optical filters, colored glass filters, narrowband interference filters, broadband interference filters, dichroic reflectors, diffraction gratings, apertures, optical fibers, or optical waveguides and the like), and one or more image sensors (e.g., charge-coupled device (CCD) sensors or cameras, complementary metal-oxide-semiconductor (CMOS) image sensors or cameras, or negative-channel metal-oxide semiconductor (NMOS) image sensors or cameras) for imaging and detection of binding of the disclosed nucleic acid binding compositions to template nucleic acid molecules tethered to a solid support or the interior of a flow cell.

Processors and computer systems: One or more processors may be employed to implement the systems for nucleic acid sequencing or other nucleic acid detection and analysis methods disclosed herein. The one or more processors may comprise a hardware processor such as a central processing unit (CPU), a graphic processing unit (GPU), a general-purpose processing unit, or computing platform. The one or more processors may be comprised of any of a variety of suitable integrated circuits (e.g., application specific integrated circuits (ASICs) designed specifically for implementing deep learning network architectures, or field-programmable gate arrays (FPGAs) to accelerate compute time, etc., and/or to facilitate deployment), microprocessors, emerging next-generation microprocessor designs (e.g., memristor-based processors), logic devices and the like. Although the disclosure is described with reference to a processor, other types of integrated circuits and logic devices may also be applicable. The processor may have any suitable data operation capability. For example, the processor may perform 512 bit, 256 bit, 128 bit, 64 bit, 32 bit, or 16 bit data operations. The one or more processors may be single core or multi core processors, or a plurality of processors configured for parallel processing.

The one or more processors or computers used to implement the disclosed methods may be part of a larger computer system and/or may be operatively coupled to a computer network (a "network") with the aid of a communication interface to facilitate transmission of and sharing of data. The network may be a local area network, an intranet and/or extranet, an intranet and/or extranet that is in communication with the Internet, or the Internet. The network in some cases is a telecommunication and/or data network. The network may include one or more computer servers, which in some cases enables distributed computing, such as cloud computing. The network, in some cases with the aid of the computer system, may implement a peer-to-peer network, which may enable devices coupled to the computer system to behave as a client or a server.

The computer system may also include memory or memory locations (e.g., random-access memory, read-only memory, flash memory, Intel® Optane™ technology), electronic storage units (e.g., hard disks), communication interfaces (e.g., network adapters) for communicating with one or more other systems, and peripheral devices, such as cache, other memory, data storage and/or electronic display adapters. The memory, storage units, interfaces and peripheral devices may be in communication with the one or more processors, e.g., a CPU, through a communication bus, e.g., as is found on a motherboard. The storage unit(s) may be data storage unit(s) (or data repositories) for storing data.

The one or more processors, e.g., a CPU, execute a sequence of machine-readable instructions, which are embodied in a program (or software). The instructions are stored in a memory location. The instructions are directed to the CPU, which subsequently program or otherwise configure the CPU to implement the methods of the present disclosure. Examples of operations performed by the CPU include fetch, decode, execute, and write back. The CPU may be part of a circuit, such as an integrated circuit. One or more other components of the system may be included in the circuit. In some cases, the circuit is an application specific integrated circuit (ASIC).

The storage unit stores files, such as drivers, libraries and saved programs. The storage unit stores user data, e.g., user-specified preferences and user-specified programs. The computer system in some cases may include one or more additional data storage units that are external to the computer system, such as located on a remote server that is in communication with the computer system through an intranet or the Internet.

Some aspects of the methods and systems provided herein may be implemented by way of machine (e.g., processor) executable code stored in an electronic storage location of the computer system, such as, for example, in the memory or electronic storage unit. The machine-executable or machine-readable code may be provided in the form of software. During use, the code is executed by the one or more processors. In some cases, the code is retrieved from the storage unit and stored in the memory for ready access by the one or more processors. In some situations, the electronic storage unit is precluded, and machine-executable instructions are stored in memory. The code may be pre-compiled and configured for use with a machine having one or more processors adapted to execute the code or may be compiled at run time. The code may be supplied in a programming language that is selected to enable the code to execute in a pre-compiled or as-compiled fashion.

Various aspects of the technology may be thought of as "products" or "articles of manufacture", e.g., "computer program or software products", typically in the form of machine- (or processor-) executable code and/or associated data that is stored in a type of machine readable medium, where the executable code comprises a plurality of instructions for controlling a computer or computer system in performing one or more of the methods disclosed herein. Machine-executable code may be stored in an optical storage unit comprising an optically readable medium such as an optical disc, CD-ROM, DVD, or Blu-Ray disc. Machine-executable code may be stored in an electronic storage unit, such as memory (e.g., read-only memory, random-access memory, flash memory) or on a hard disk. "Storage" type media include any or all of the tangible memory of the computers, processors or the like, or associated modules thereof, such as various semiconductor memory chips, optical drives, tape drives, disk drives and the like, which may provide non-transitory storage at any time for the software that encodes the methods and algorithms disclosed herein.

All or a portion of the software code may at times be communicated via the Internet or various other telecommunication networks. Such communications, for example, enable loading of the software from one computer or processor into another, for example, from a management server or host computer into the computer platform of an application server. Thus, other types of media that are used to convey the software encoded instructions include optical, electrical and electromagnetic waves, such as those used across physical interfaces between local devices, through wired and optical landline networks, and over various atmospheric links. The physical elements that carry such waves, such as wired or wireless links, optical links, or the like, are also considered media that convey the software encoded instructions for performing the methods disclosed herein. As used herein, unless restricted to non-transitory, tangible "storage" media, terms such as computer or machine "readable medium" refer to any medium that participates in providing instructions to a processor for execution.

The computer system typically includes, or may be in communication with, an electronic display for providing, for example, images captured by a machine vision system. The display is typically also capable of providing a user interface (UI). Examples of UI's include but are not limited to graphical user interfaces (GUIs), web-based user interfaces, and the like.

System control software: In some instances, the disclosed systems may comprise a computer (or processor) and computer-readable media that includes code for providing a user interface as well as manual, semi-automated, or fully-automated control of all system functions, e.g. control of a fluid flow controller and/or fluid dispensing system (or subsystem), a temperature control system (or sub-system), an imaging system (or sub-system), etc. In some instances, the system computer or processor may be an integrated component of the instrument system (e.g. a microprocessor or mother board embedded within the instrument). In some instances, the system computer or processor may be a stand-alone module, for example, a personal computer or laptop computer. Examples of fluid flow control functions that may be provided by the instrument control software include, but are not limited to, volumetric fluid flow rates, fluid flow velocities, the timing and duration for sample and reagent additions, rinse steps, and the like. Examples of temperature control functions that may be provided by the instrument control software include, but are not limited to, specifying temperature set point(s) and control of the timing, duration, and ramp rates for temperature changes. Examples of imaging system control functions that may be provided by the instrument control software include, but are not limited to, autofocus capability, control of illumination or excitation light exposure times and intensities, control of image acquisition rate, exposure time, data storage options, and the like.

Image processing software: In some instances of the disclosed systems, the system may further comprise computer-readable media that includes code for providing image processing and analysis capability. Examples of image processing and analysis capability that may be provided by the software include, but are not limited to, manual, semi-automated, or fully-automated image exposure adjustment (e.g. white balance, contrast adjustment, signal-averaging and other noise reduction capability, etc.), manual, semi-automated, or fully-automated edge detection and object identification (e.g., for identifying clusters of amplified template nucleic acid molecules on a substrate surface), manual, semi-automated, or fully-automated signal intensity measurements and/or thresholding in one or more detection channels (e.g., one or more fluorescence emission channels), manual, semi-automated, or fully-automated statistical analysis (e.g., for comparison of signal intensities to a reference value for base-calling purposes).

In some instances, the system software may provide integrated real-time image analysis and instrument control, so that sample loading, reagent addition, rinse, and/or imaging/base-calling steps may be prolonged, modified, or repeated as necessary until, e.g., optimal base-calling results are achieved. Any of a variety of image processing and analysis algorithms known to those of skill in the art may be used to implement real-time or post-processing image analysis capability. Examples include, but are not limited to, the Canny edge detection method, the Canny-Deriche edge detection method, first-order gradient edge detection methods (e.g. the Sobel operator), second order differential edge detection methods, phase congruency (phase coherence) edge detection methods, other image segmentation algorithms (e.g. intensity thresholding, intensity clustering methods, intensity histogram-based methods, etc.), feature and pattern recognition algorithms (e.g. the generalized Hough transform for detecting arbitrary shapes, the circular Hough transform, etc.), and mathematical analysis algorithms (e.g. Fourier transform, fast Fourier transform, wavelet analysis, auto-correlation, etc.), or combinations thereof.

In some instances, the system control and image processing/analysis software may be written as separate software modules. In some instances, the system control and image processing/analysis software may be incorporated into an integrated software package.

Nucleic acid sequencing and analysis applications: The disclosed compositions, reagents, and methods may be used for any of a variety of nucleic acid sequencing and analysis applications. Examples include, but are not limited to, DNA sequencing, RNA sequencing, whole genome sequencing, targeted sequencing, exome sequencing, genotyping, and the like.

In some instances, the disclosed methods of determining the sequence of a nucleic acid molecule comprise: a) contacting a double-stranded or partially double-stranded nucleic acid molecule comprising a template strand to be sequenced and a complementary strand to be elongated with one or more of the disclosed nucleic acid binding compositions; and b) detecting the binding of a nucleic acid binding composition to the nucleic acid molecule, thereby determining the presence of one of said one or more nucleic acid binding compositions on said nucleic acid molecule and the identity of the next nucleotide (i.e., the N+1 or terminal nucleotide) to be incorporated into the complementary strand. In some instances, the method may further comprise incorporating the N+1 or terminal nucleotide into the complementary strand, and then repeating the contacting, detecting, and incorporating steps for one or more additional iterations, thereby determining the sequence of the template strand of the nucleic acid molecule.

In some instances, the nucleic acid molecule is tethered to the surface of a solid support, e.g., through hybridization of the template strand to an adapter nucleic acid sequence or primer nucleic acid sequence that is tethered to the solid support. In some instances, the solid support comprises a glass, fused-silica, silicon, or polymer substrate. In some instances, the solid support comprises a low non-specific binding coating comprising one or more hydrophilic polymer layers (e.g. PEG layers). In some instances, at least one of the hydrophilic polymer layers comprises a branched polymer molecule (e.g., a branched PEG molecule comprising, e.g., 4, 8, 16, or 32 branches). Examples of such low non-specific binding supports are described in co-pending U.S. patent application Ser. No. 16/363,842, which is incorporated herein by reference in its entirety.

In some embodiments, the solid support comprises oligonucleotide adapters or primers tethered to at least one hydrophilic polymer layer at a surface density ranging from about 1,000 primer molecules per $\mu m^2$ to about 1,000,000 primer molecules per $\mu m^2$. In some instances, the surface density of oligonucleotide primers may be at least 1,000, at least 2,000, at least 3,000, at least 4,000, at least 5,000, at least 10,000, at least 20,000, at least 30,000, at least 40,000, at least 50,000, at least 60,000, at least 70,000, at least 80,000, at least 90,000, at least 100,000, at least 200,000, at least 300,000, at least 400,000, at least 500,000, at least 600,000, at least 700,000, at least 800,000, at least 900,000, or at least 1,000,000 molecules per $\mu m^2$. In some instances, the surface density of oligonucleotide primers may be at most 1,000,000, at most 900,000, at most 800,000, at most 700,000, at most 600,000, at most 500,000, at most 400,000, at most 300,000, at most 200,000, at most 100,000, at most 90,000, at most 80,000, at most 70,000, at most 60,000, at most 50,000, at most 40,000, at most 30,000, at most 20,000, at most 10,000, at most 5,000, at most 4,000, at most 3,000, at most 2,000, or at most 1,000 molecules per $\mu m^2$. Any of the lower and upper values described in this paragraph may be combined to form a range included within the present disclosure, for example, in some instances the surface density of primers may range from about 10,000 molecules per $\mu m^2$ to about 100,000 molecules per $\mu m^2$. Those of skill in the art will recognize that the surface density of primer molecules may have any value within this range, e.g., about 455,000 molecules per μm².

In some instances, template nucleic acid molecules or fragments thereof may be hybridized to oligonucleotide adapters or primers tethered on the surface of a solid support. In some instances, template nucleic acid molecules or fragments thereof may be clonally-amplified after the initial hybridization to oligonucleotide adapters or primers tethered on the surface of a solid support, e.g., to create clones or clusters of identical template nucleic acid molecules or fragments thereof. In some instances, the clonal amplification may be performed using a polymerase chain reaction (PCR), multiple displacement amplification (MDA), transcription-mediated amplification (TMA), nucleic acid sequence-based amplification (NASBA), strand displacement amplification (SDA), real-time SDA, bridge amplification, isothermal bridge amplification, rolling circle amplification, circle-to-circle amplification, helicase-dependent amplification, recombinase-dependent amplification, single-stranded binding (SSB) protein-dependent amplification, or any combination thereof.

In some instances, the surface density of clonally-amplified template nucleic acid colonies (or clusters) may range from about from about 100 colonies per mm² to about $1 \times 10^{12}$ colonies per mm². In some instances, the surface density of clonally-amplified colonies may be at least 100, at least 500, at least 1,000, at least 5,000, at least 10,000, at least 15,000, at least 20,000, at least 25,000, at least 30,000, at least 35,000, at least 40,000, at least 45,000, at least 50,000, at least 55,000, at least 60,000, at least 65,000, at least 70,000, at least 75,000, at least 80,000, at least 85,000, at least 90,000, at least 95,000, at least 100,000, at least 150,000, at least 200,000, at least 250,000, at least 300,000, at least 350,000, at least 400,000, at least 450,000, at least 500,000, at least 550,000, at least 600,000, at least 650,000, at least 700,000, at least 750,000, at least 800,000, at least 850,000, at least 900,000, at least 950,000, at least 1,000,000, at least 5,000,000, at least $1 \times 10^7$, at least $5 \times 10^7$, at least $1 \times 10^8$, at least $5 \times 10^8$, at least $1 \times 10^9$, at least $5 \times 10^9$, at least $1 \times 10^{10}$, at least $5 \times 10^{10}$, at least $1 \times 10^{11}$, at least $5 \times 10^{11}$, or at least $1 \times 10^{12}$ colonies per mm². In some instances, the surface density of clonally-amplified colonies may be at most $1 \times 10^{12}$, at most $5 \times 10^{11}$, at most $1 \times 10^{11}$, at most $5 \times 10^{10}$, at most $1 \times 10^{10}$, at most $5 \times 10^9$, at most $1 \times 10^9$, at most $5 \times 10^8$, at most $1 \times 10^8$, at most $5 \times 10^7$, at most $1 \times 10^7$, at most 5,000,000, at most 1,000,000, at most 950,000, at most 900,000, at most 850,000, at most 800,000, at most 750,000, at most 700,000, at most 650,000, at most 600,000, at most 550,000, at most 500,000, at most 450,000, at most 400,000, at most 350,000, at most 300,000, at most 250,000, at most 200,000, at most 150,000, at most 100,000, at most 95,000, at most 90,000, at most 85,000, at most 80,000, at most 75,000, at most 70,000, at most 65,000, at most 60,000, at most 55,000, at most 50,000, at most 45,000, at most 40,000, at most 35,000, at most 30,000, at most 25,000, at most 20,000, at most 15,000, at most 10,000, at most 5,000, at most 1,000, at most 500, or at most 100 colonies per mm². Any of the lower and upper values described in this paragraph may be combined to form a range included within the present disclosure, for example, in some instances the surface density of clonally-amplified colonies may range from about 5,000 colonies per mm² to about 50,000 colonies per mm². Those of skill in the art will recognize that the surface density of clonally-amplified colonies may have any value within this range, e.g., about 48,800 colonies per mm².

In some instances, the sequencing reaction cycle comprising the contacting, detecting, and incorporating steps is performed in a total time ranging from about 5 minutes to about 60 minutes. In some instances, the sequencing reaction cycle is performed in at least 5 minutes, at least 10 minutes, at least 20 minutes, at least 30 minutes, at least 40 minutes, at least 50 minutes, or at least 60 minutes. In some instances, the sequencing reaction cycle is performed in at most 60 minutes, at most 50 minutes, at most 40 minutes, at most 30 minutes, at most 20 minutes, at most 10 minutes, or at most 5 minutes. Any of the lower and upper values described in this paragraph may be combined to form a range included within the present disclosure, for example, in some instances the sequencing reaction cycle may be performed in a total time ranging from about 10 minutes to about 30 minutes. Those of skill in the art will recognize that the sequencing cycle time may have any value within this range, e.g., about 16 minutes.

In some instances, the disclosed compositions and methods for nucleic acid sequencing will provide an average base-calling accuracy of at least 80%, at least 85%, at least 90%, at least 92%, at least 94%, at least 96%, at least 98%, at least 99%, at least 99.5%, at least 99.8%, or at least 99.9% correct over the course of a sequencing run. In some instances, the disclosed compositions and methods for nucleic acid sequencing will provide an average base-calling accuracy of at least 80%, at least 85%, at least 90%, at least 92%, at least 94%, at least 96%, at least 98%, at least 99%, at least 99.5%, at least 99.8%, or at least 99.9% correct per every 1,000 bases, 10,0000 bases, 25,000 bases, 50,000 bases, 75,000 bases, or 100,000 bases called.

In some instances, the disclosed compositions and methods for nucleic acid sequencing will provide an average Q-score for base-calling accuracy over a sequencing run that ranges from about 20 to about 50. In some instances, the average Q-score is at least 20, at least 25, at least 30, at least 35, at least 40, at least 45, or at least 50. Those of skill in the art will recognize that the average Q-score may have any value within this range, e.g., about 32.

In some instances, the disclosed compositions and methods for nucleic acid sequencing will provide a Q-score of greater than 30 for at least 80%, at least 85%, at least 90%, at least 95%, at least 98%, or at least 99% of the terminal (or N+1) nucleotides identified.

In some instances, the disclosed compositions and methods for nucleic acid sequencing will provide a Q-score of greater than 35 for at least 80%, at least 85%, at least 90%, at least 95%, at least 98%, or at least 99% of the terminal (or N+1) nucleotides identified.

In some instances, the disclosed compositions and methods for nucleic acid sequencing will provide a Q-score of greater than 40 for at least 80%, at least 85%, at least 90%, at least 95%, at least 98%, or at least 99% of the terminal (or N+1) nucleotides identified.

In some instances, the disclosed compositions and methods for nucleic acid sequencing will provide a Q-score of greater than 45 for at least 80%, at least 85%, at least 90%, at least 95%, at least 98%, or at least 99% of the terminal (or N+1) nucleotides identified.

In some instances, the disclosed compositions and methods for nucleic acid sequencing will provide a Q-score of greater than 50 for at least 80%, at least 85%, at least 90%, at least 95%, at least 98%, or at least 99% of the terminal (or N+1) nucleotides identified.

EXAMPLES

These examples are provided for illustrative purposes only and not to limit the scope of the claims provided herein.

Figure 7:
FIG. 7 provides a schematic illustration of the structure of a nucleotide-tethered Bsu polymerase created using different conjugation chemistries.
Figure 7:
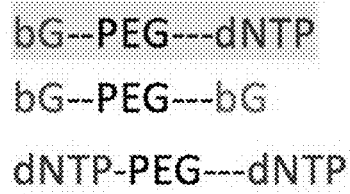
Figure 7:
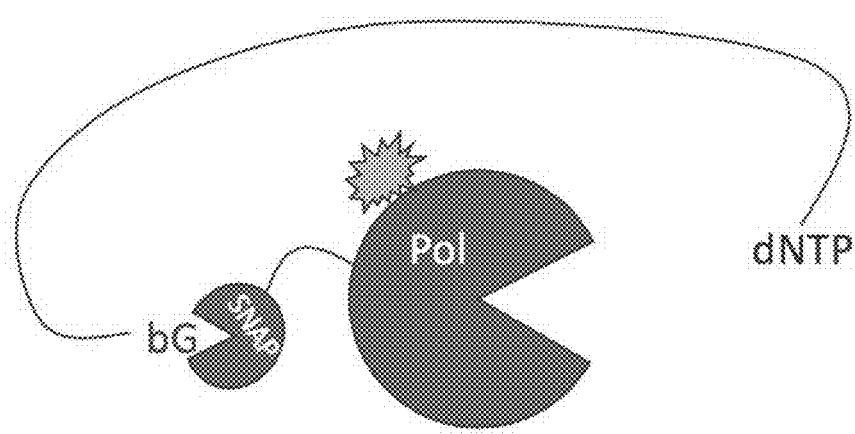

Example 1: Fluorescently labeled Bsu polymerase was conjugated to an azido-blocked dNTP via a PEG-10K Dalton linker. The linker was first conjugated to the azide-blocked dNTP using an amine-carboxyl (NHS-COOH) linkage. The linker was then functionalized at the end opposite the azido-blocked dNTP with a benzylguanosine group (bG) using an amide (NHS-NH2) linkage. The benzylguanosine group was then bound to a SNAP-tag fused to the N-terminus of the polymerase. This process was repeated for all four dNTPs and yielded nucleotide-tethered Bsu polymerase as shown in FIG. 7. Similar coupling chemistries may be used to form PEG linker complexes comprising a benzylguanosine group at each end, or a dNTP at each end, as illustrated. The length of the linker varies depend on the type of nucleotide tethered to the polymerase.

Example 2: Fluorescently labeled Bsu polymerase was conjugated to an azido-blocked dNTP via a PEG-10K Dalton linker. The linker was first conjugated to the azide-blocked dNTP using an amine-carboxyl (NHS-COOH) linkage. The linker was then functionalized at the end opposite the azido-blocked dNTP with a benzylguanosine (bG) group using thiol-maleimide chemistry to produce a disulfide linkage. The benzylguanosine group was then bound to a SNAP-tag fused to the N terminus of the polymerase. This process was repeated for all four dNTPs and yielded nucleotide-tethered Bsu polymerase as shown in FIG. 7.

Example 3: Fluorescently labeled Bsu polymerase was conjugated to an azido-blocked dNTP via a PEG-10K Dalton linker. The linker was conjugated at one end with an azido-blocked dNTP, and at the end opposite the azido-blocked dNTP with a benzylguanosine group, using an amide (NHS-NH2) linkage, with both conjugation events occurring in a single reaction mixture. The benzylguanosine group was then bound to a SNAP-tag fused to the N-terminus of the polymerase. This process was repeated for all four dNTPs and yielded nucleotide-tethered Bsu polymerase as shown in FIG. 7.

Figure 8:
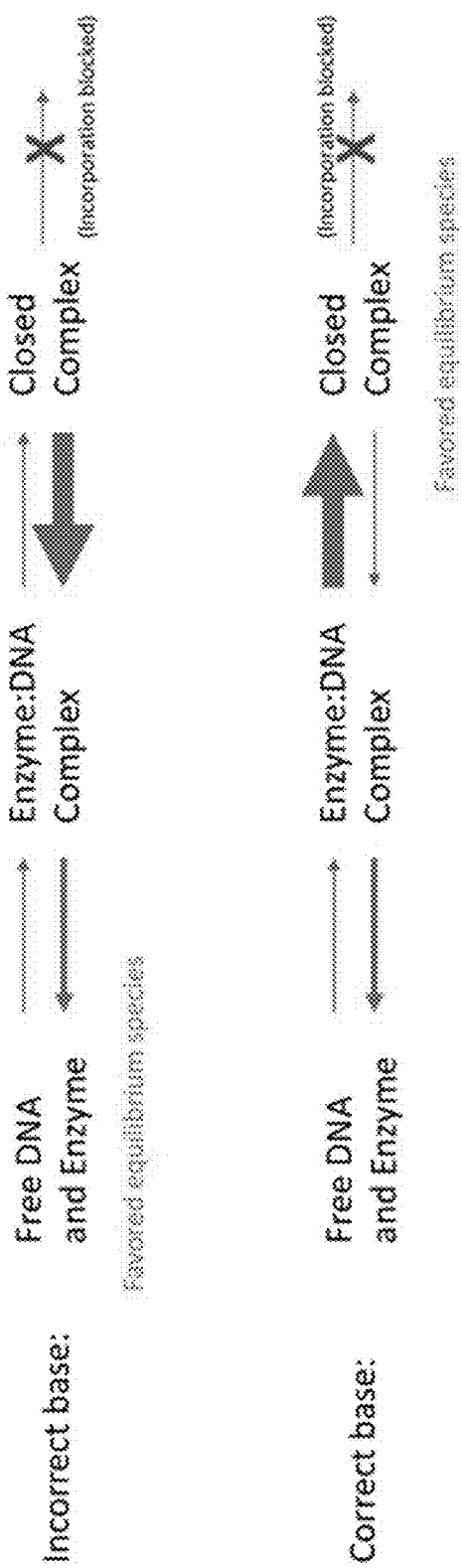
FIG. 8 provides a kinetic mechanism for base-selective polymerase binding to primed nucleic acid substrates utilizing tethered nucleotide constructs.
Figure 9:
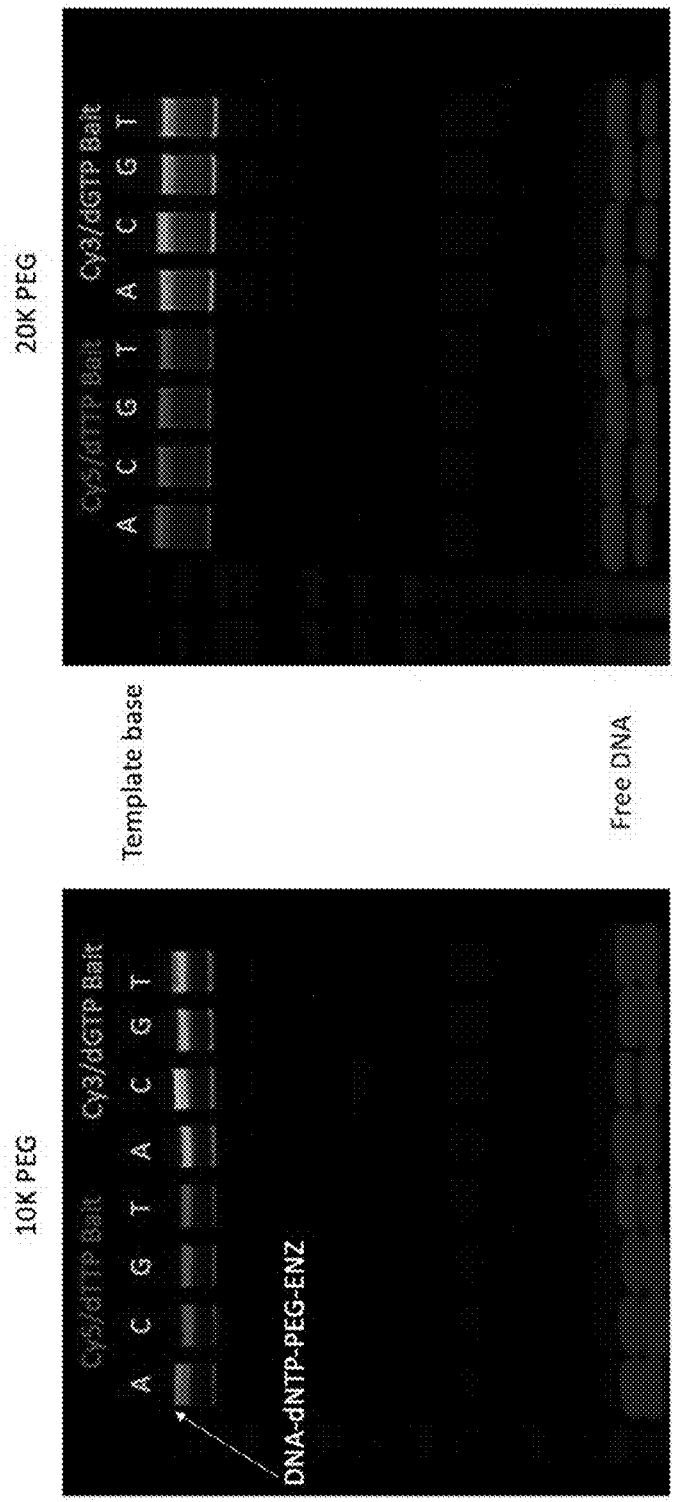
FIG. 9 shows non-limiting examples of data illustrating the use of polymerase-nucleotide conjugates to identify the N+1 base in a sequencing-by-incorporation reaction. Conjugates comprising a deoxythymidine triphosphate (dTTP) moiety show clear discrimination in constructs utilizing 10K Dalton PEG linkers (left panel, lane 1), but markedly reduced binding with 20K Dalton PEG linkers (right panel, lanes 1-4). By contrast, conjugates comprising a deoxyguanosine triphosphate (dGTP) moiety show significant binding with reduced base discrimination in constructs utilizing 10K Dalton PEG linkers (left panel, lanes 6 and 8), with enhanced base discrimination in constructs utilizing 20K Dalton PEG linkers (right panel, lane 6).

Example 4: FIG. 8 provides an illustration of a kinetic mechanism for base-selective polymerase binding to primed nucleic acid substrates utilizing tethered nucleotide constructs. Fluorescently labeled Bsu polymerase conjugated to dNTP as in Example 1 was bound to primed, single stranded DNA and subjected to agarose gel electrophoresis to determine whether the N+1 base could be identified uniquely using this reagent. Two different nucleotides were used corresponding to two different fluorescent labels: dTTP, labeled with Cy5 (red); and dGTP, labeled with Cy3 (green). As shown in FIG. 9, the nucleotide linked polymerase reagent was clearly able to identify the N+1 base using defined substrates. Unexpectedly and importantly, the linker length required to obtain base discrimination was different between the two nucleotides: Tethered dTTP moieties show clear discrimination in constructs utilizing 10K Dalton PEG linkers (FIG. 9, left panel, lane 1), but markedly reduced binding with 20K Dalton PEG linkers (FIG. 9, right panel, lanes 1-4). By contrast, tethered dGTP moieties show significant binding with reduced base discrimination in constructs utilizing 10K Dalton PEG linkers (FIG. 9, left panel, lanes 6 and 8), with enhanced base discrimination in constructs utilizing 20K Dalton PEG linkers (FIG. 9, right panel, lane 6).

Figure 10:
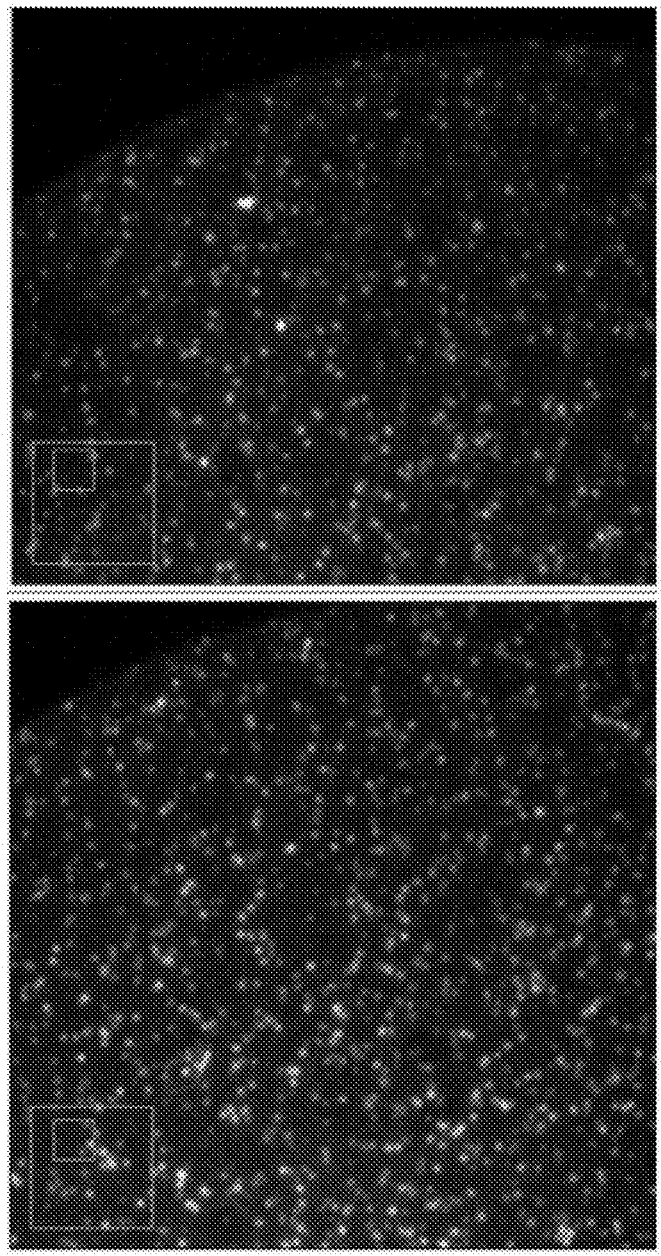
FIG. 10 provides a non-limiting example of image data illustrating two cycles of a sequencing reaction performed using polynucleotides tethered to a substrate surface, including the cleavage of a linkage between a dNTP moiety and a Bsu polymerase and subsequent incorporation of the released dNTP (dTTP, red, and dGTP, green).

Example 5: Fluorescently labeled Bsu polymerase conjugated to dNTP as in Example 1 was bound to immobilized, primed, single stranded DNA and cleaved to determine whether the base provided by the reagents described herein could be released from the complex after visualization in order to be incorporated into the growing nucleic acid chain, and thus continue the sequencing reaction. FIG. 10 provides a non-limiting example of image data illustrating two cycles of a sequencing reaction performed using polynucleotides tethered to a substrate surface, including the cleavage of a linkage between a dNTP moiety and a Bsu polymerase and subsequent incorporation of the released dNTP (dTTP, red, and dGTP, green). As shown in FIG. 10, cleavage using tetrahydropyran (THP) at 55° C. led to the incorporation of the labeled nucleotide into the elongating chain. Attachment of nucleotides using disulfide or acid labile linkers to allow incorporation of tethered nucleotides using alternative cleavage chemistries is also contemplated.

Figure 11:
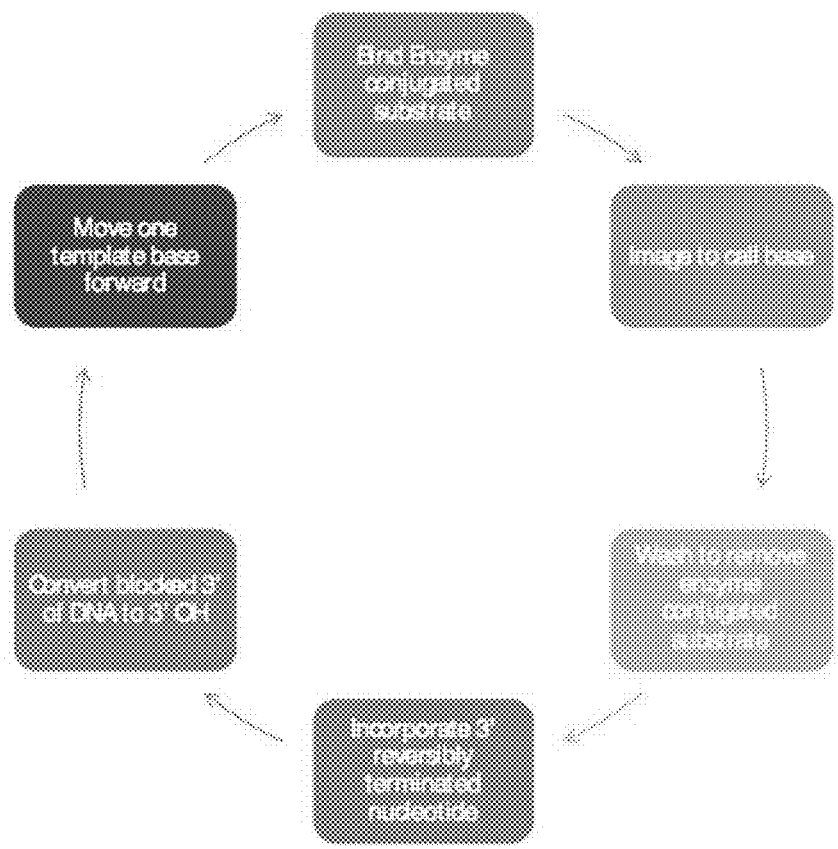
FIG. 11 illustrates a representative sequencing reaction cycle according to the methods disclosed herein.

Example 6: FIG. 11 illustrates a representative sequencing reaction cycle using the disclosed polymerase-nucleotide conjugates. Fluorescently labeled Bsu polymerase conjugated to dNTP as in Example 1 was bound to immobilized, primed, single stranded DNA and imaged to determine whether the N+1 base could be identified uniquely using this reagent. Two different nucleotides were used corresponding to two different fluorescent labels: dTTP, labeled with Cy5 (red); and dGTP, labeled with Cy3 (green). As demonstrated in the images shown in FIG. 12A, the nucleotide linked polymerase reagent was clearly able to distinguish between different spots. Principal component analysis of each spot shows clear differentiation between green and red signals with little or no within-spot overlap (FIG. 12B).

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in any combination in practicing the invention. It is intended that the following claims define the scope of the invention and that methods and structures within the scope of these claims and their equivalents be covered thereby.

What is claimed is:

1. A system for identifying a nucleotide, the system comprising:
   (a) a nucleic acid binding composition comprising:
      (i) a nucleic acid binding moiety comprising a polymerase or a catalytic domain thereof;
      (ii) a base-pairing moiety, wherein the base-pairing moieties is connected to the nucleic acid binding moiety via a linker, and wherein the linker has a length effective to allow the base-pairing moiety to pair with a complementary nucleotide in a primed polynucleotide while precluding incorporation of the base-pairing moiety into a 3' end of the primed polynucleotide, wherein the primed polynucleotide is unlabeled when the primed polynucleotide is disassociated from the base-pairing moiety, wherein:
         (A) the polymerase or the catalytic domain thereof comprises a point mutation that renders the polymerase or the catalytic domain thereof incapable of incorporating any nucleotide into the 3' end of the primed polynucleotide; or
         (B) the nucleic acid binding composition lacks sufficient magnesium to render the polymerase or the catalytic domain thereof incapable of incorporating any nucleotide into the 3' end of the primed polynucleotide; and
      (iii) a detectable label coupled to the nucleic acid binding moiety, the base-pairing moiety, or the linker; and (b) an imaging module comprising an optical waveguide, wherein the imaging module is configured to detect the nucleic acid binding composition bound to the complementary nucleotide in the primed polynucleotide, thereby identifying the complementary nucleotide.

2. The system of claim 1, wherein the base-pairing moiety comprises a nucleotide or nucleotide analog.

3. The system of claim 1, wherein the polymerase or the catalytic domain thereof is a reverse transcriptase, or a catalytic domain thereof.

4. The system of claim 1, wherein the linker comprises a nucleic acid, a peptide, or a polymer.

5. The system of claim 1, wherein the linker comprises Polyethylene glycol (PEG), and wherein the PEG has an average molecular weight of between about 5 kilodaltons (kDa) and about 20 kDa.

6. The system of claim 2, wherein the nucleotide or nucleotide analog is conjugated to the linker through the 5' end of the nucleotide or nucleotide analog.

7. The system of claim 2, wherein the nucleotide or nucleotide analog comprises a deoxyribonucleotide, a ribonucleotide, a deoxyribonucleoside, or a ribonucleoside.

8. The system of claim 2, wherein the nucleotide or nucleotide analog has been modified to inhibit elongation during a polymerase reaction or a sequencing reaction.

9. The system of claim 2, wherein the nucleotide or nucleotide analog lacks a hydroxyl group at a 3' position of a sugar of the nucleotide or nucleotide analog.

10. The system of claim 2, wherein the nucleotide or nucleotide analog is modified to contain a blocking group at a 3' position of a sugar of the nucleotide or nucleotide analog.

11. The system of claim 1, wherein the nucleic acid binding composition further comprises one or more detectable labels.

12. The system of claim 1, wherein the nucleic acid binding composition further comprises one or more fluorescent labels.

13. A system for identifying a nucleotide, the system comprising:
 (a) a nucleic acid binding composition comprising:
  (i) at least one nucleic acid binding moiety comprising a polymerase or a catalytic domain thereof;
  (ii) at least four different nucleotides or nucleotide analogs,
   wherein each of the at least one nucleic acid binding moieties is tethered to one of the at least four different nucleotides or nucleotide analogs via a linker,
  wherein a length of the linker is different for each of the at least four different nucleotides or nucleotide analogs; and
  (iii) a detectable label coupled to the nucleic acid binding moiety or the linker,
   wherein a nucleotide or a nucleotide analog of the at least four different nucleotides or nucleotide analogs is configured to couple with a complementary nucleotide in a primed polynucleotide, wherein the primed polynucleotide is unlabeled when the primed polynucleotide is disassociated from nucleic acid binding composition, and wherein:
  (A) the polymerase or the catalytic domain thereof comprises a point mutation that renders the polymerase or the catalytic domain thereof incapable of incorporating any nucleotide into a 3' end of the primed polynucleotide; or
  (B) the nucleic acid binding composition lacks sufficient magnesium, to render the polymerase or the catalytic domain thereof incapable of incorporating any nucleotide into a 3' end of the primed polynucleotide; and
 (b) an imaging module comprising an optical waveguide, wherein the imaging module is configured to detect the nucleic acid binding composition coupled to the complementary nucleotide in the primed polynucleotide, thereby identifying the complementary nucleotide.

14. The system of claim 13, wherein one of the at least four different nucleotides or nucleotide analogs comprises a ribonucleotide or a ribonucleoside.

15. The system of claim 13, wherein the length of the linker is between 1 nanometer (nm) and 1,000 nm.

* * * * *